(12) United States Patent
Schipper

(10) Patent No.: US 7,105,485 B2
(45) Date of Patent: Sep. 12, 2006

(54) HO-1 SUPPRESSOR AS A DIAGNOSTIC AND PROGNOSTIC TEST FOR DEMENTING DISEASES

(75) Inventor: Hyman M. Schipper, 5785 Einstein, Montreal, Quebec (CA) H4W 2Y9

(73) Assignees: The Sir Mortimer B. Davis - Jewish General Hospital, Montreal (CA); Hyman M. Schipper, Montreal (CA)

( * ) Notice: Subject to any disclaimer, the term of this patent is extended or adjusted under 35 U.S.C. 154(b) by 357 days.

(21) Appl. No.: 10/333,880

(22) PCT Filed: Jul. 25, 2001

(86) PCT No.: PCT/CA01/01066

§ 371 (c)(1),
(2), (4) Date: Jul. 28, 2003

(87) PCT Pub. No.: WO02/08449

PCT Pub. Date: Jan. 31, 2002

(65) Prior Publication Data

US 2004/0033563 A1 Feb. 19, 2004

Related U.S. Application Data

(60) Provisional application No. 60/220,813, filed on Jul. 25, 2000.

(51) Int. Cl.
*A16K 61/00* (2006.01)
*C07K 1/00* (2006.01)
*C12P 21/06* (2006.01)

(52) U.S. Cl. ..................... 514/12; 530/350; 435/69.1
(58) Field of Classification Search ................ 530/350; 435/69.1; 514/12
See application file for complete search history.

(56) References Cited

OTHER PUBLICATIONS

Abraham, N.G. "Quantitation of heme oxygenase (HO-1) copies in human tissue or body fluids by competitive RT/PCR", in Methods in Molecular Biology, (1998) vol. 108: *Free Radical and Antioxidant Protocols* (Armstrong, D., ed.),pp. 199-209, Humana Press Inc., Totowa, NF.

Abraham, N.G., et al., *Cell Physiol. Biochem.*, (1996), 129-168.

Applegate, L.A., et al., "Induction of heme oxygenase: a general response to oxidant stress in cultured mammalian cells" *Cancer Res.*, (1991), Feb. 1;51(3):974-978.

Balldin J., et al., "Dexamethasone suppression test and serum prolactin in dementia disorders.", *Psychiatry* Sep. 1983;143:277-81.

Beal, M.F., "Does impairment of energy metabolism result in excitotoxic neuronal death in neurodegenerative illnesses?", *Ann. Neurol.* Feb. 1992;31(2):119-30.

Benzi, G. and Moretti, A., "Are reactive oxygen species involved in Alzheimer's disease?", *Neurobiol. Aging* Jul.-Aug. 1995;16, 4:661-674.

Berg, L., "Clinical dementia rating (CDR)" *Psychopharmacology Bulletin*, (1988), 24, pp. 637-639.

Blackford, R.C. and LaRue, A., "Criteria for diagnosing age-associated memory impairment: proposed improvements from the field" *Dev. Neuropsychol.*, (1989), 5:295-306.

Chertkow, H. and Bergman, H. "Troubles cognitifs et diagnostic precoce de la demance" In, M. Arcand & R. Hebert (Eds.), *Precis pratique de geriatrie* (2e ed.) Ste-Hyacinthe/Paris: Edisem/Maloine, (1997) pp. 157-172.

Chomczynski P. and Sacchi N. "Single-step method of RNA isolation by acid guanidinium thiocyanate-phenol-chloroform extraction" *Analytical Biochem.* (1987) 162:156-159.

Chomczynski, P., et al. "DNAzol: a reagent for the rapid isolation of genomic DNA." *Biotechniques* Mar. 1997;22(3):550-3.

Chopra, V.S., et al. "A cellular stress model for the differential expression of glial lysosomal cathepsins in the aging nervous system" *Exp. Neurol.* Oct. 1997;147(2):221-228.

Chopra, V.S., et al. "Differential effects of cysteamine on heat shock protein induction and cytoplasmic granulation in astrocytes and glioma cells" *Mol. Brain Res.* Jul. 1995;31(1-2):173-184.

Church G.M. and Gilbert W. "Genomic sequencing" *Proc. Natl. Acad. Sci. USA* (1984) 81:1991-1995.

Crook, T., et al., "Age-associated memory impairment: proposed diagnostic criteria and measures of clinical change: report of a National Institute of Mental Health work group" *Dev. Neuropsychol.* (1986) 2:261-276.

Davis, R.E., et al., *Neurology* (1996) A276.

Dawe, B., et al., "Concepts of mild memory impairment in the elderly and their relationship to dementia—a review" *Intl. J. Geriat. Psychiatry* (1992) 7:473-479.

de Leon, M.J., et al., "Abnormal cortisol response in Alzheimer's disease linked to hippocampal atrophy." *Lancet* Aug. 13, 1988;2(8607):391-392.

(Continued)

*Primary Examiner*—Maryam Monshipouri

(57) ABSTRACT

The invention relates to an improved method for predicting the onset of, diagnosing, prognosticating and/or treating dementing diseases. The method comprises determining the level of heme oxygenase-1 suppressor (HOS) activity and/or factor in tissue or body fluid obtained from a patient, and comparing said level with the corresponding level of HOS activity and/or factor in corresponding tissue or body fluid obtained from at least one control person. The tissue or body fluid is suitably blood, plasma, lymphocytes, cerebrospinal fluid, urine, saliva, epithelia or fibroblasts. The method is useful where the dementing disease is any of Alzheimer Disease, Age-Associated Cognitive Decline, Mild Cognitive Impairment, Parkinson disease with dementia, Progressive Supranuclear Palsy, Vascular (i.e. multi-infarct) Dementia, Lewy Body Dementia, Huntington's Disease, Down's syndrome, normal pressure hydrocephalus, corticobasal ganglionic degeneration, multisystem atrophy, head trauma, neurosyphilis, Creutzfeld-Jacob disease and other prion diseases, HIV and other encephalitides, and metabolic disorders such as hypothyroidism and vitamin B12 deficiency. The method may also prove useful in differentiating the "pseudodementia" of depression from Alzheimer disease.

15 Claims, 13 Drawing Sheets

OTHER PUBLICATIONS

Deramaudt, T.B., et al. "Negative regulation of human heme oxygenase in microvessel endothelial cells by dexamethasone" *Proc. Soc. Exp. Biol. Med.* Nov. 1999;222(2):185-193.

El-Ghar, S. Abo, et al., "Oxygen Free Radicals and Alzheimer Disease" *Can. J. Neurol. Sci.* 22 (suppl. 1) S69, 1995 (Abst. #P133).

Famulari, A.L., et al., "The antioxidant enzymatic blood profile in Alzheimer's and vascular diseases. Their association and a possible assay to differentiate demented subjects and controls." *J. Neurological Sciences* Sep. 15, 1996;141(1-2):69-78.

Farlow, M., et al., *Lancet* (1992) 340:453-454.

Feinberg AP and Vogelstein B. "A Technique for radiolabelling DNA restriction endonuclease fragments to high specific activity" *Analytic Biochem.* (1984) 137:266-267.

Feldman, H. "Diagnosis of Alzheimer's Disease" *Oral Presentation at the Royal College of Medicine meeting* Sep. 1997 Vancouver, B.C. (no printed publication available).

Fillenbaum, G.G. and Smyer, M.A. "The development, validity, and reliability of the OARS multidimensional functional assessmane questionaire" *J. Gerentology* (1981) 36:428-434.

Fujiwara Noriko, et al. "Quinazoline derivatives suppress nitric oxide production by macrophages through inhibition of NOS II gene expression", *FEBS Letters* Oct. 21, 1996;395(2-3):299-303.

Fukuyama, R., et al., "Gene expression of ND4, a subunit of complex I of oxidative phosphorylation in mitochondria, is decreased in temporal cortex of brains of Alzheimer's disease patients." *Brain Res.* Mar. 25, 1996;713(1-2):290-3.

Grossi, D., et al. "Senile dementias" *II International Symposium* (1988) Paris: John Libbey Eurotext. pp. 97-99.

Haxby J.V, et al. "Individual trajectories of cognitive decline in patients with dementia of the Alzheimer type" *J. Clin. Exp. Neuropsychol.*Jul. 1992;14(4):575-592.

Hughes, C.P., et al., "A new clinical scale for the staging of dementia" *Br. J. Psychiatry* (1982) 140:566-572.

Ihara N., et al. "Developmental changes of gene expression in heme metabolic enzymes in rat placenta" *FEBS Letter* (1998)439:163-167.

Kennard, M.L., et al., "Serum levels of the iron binding protein p97 are elevated in Alzheimer's disease" *Nature Medicine* Nov. 1996;2(11):1230-1235.

Keyse, S.M., et al. "Heme oxygenase is the major 32-kDa stress protein induced in human skin fibroblasts by UVA radiation, hydrogen peroxide, and sodium arsenite" *PNAS*, (1989), 86:99-103.

Kral, V.A., "Senescent forgetfulness: benign and malignant" *J. Can. Med. Assoc.* (1962) 86:257-260.

Kutty R. Krishnan, et al. "Induction of heme oxygenase 1 in the retina by intense visible light: Suppression by the antioxidant dimethylthiourea", *PNAS*, (1995):1177-1181.

Lannfelt, L., et al., "Decreased alpha-secretase-cleaved amyloid precursor protein as a diagnostic marker for Alzheimer's disease." *Nature Med.* Aug. 1995;1(8):829-832.

Lavrosky, Y., et al. "Downregulation of the human heme oxygenase gene by glucocorticoids and identification of 56b regulatory elements" *Biochem. Biophys. Res. Comm.* (1996) 218:759-765.

Levy, R., "Aging-associated cognitive decline. Working Party of the International Psychogeriatric Association in collaboration with the World Health Organization." *International Psychogeriatrics* (1994) Spring;6:63-68.

Mann, U., et al. "Heterogeneity in Alzheimer's disease: Progression rate segregated by distinct neuropsychological and cerebral metabolic profiles" *J. Neurol. Neurosurg. Psychiatry* (1992) 55:956-959.

Masuya Yoshiro, et al. "Involvement of the tyrosine phosphorylation pathway in induction of human heme oxygenase-1 by hemin, sodium arsenite, and cadmium chloride" *Biochemistry*, (1998)124:628-633.

Mawal Yogesh R., et al., "RT-PCR demonstration of supressed lymphocyte HO-1 mRNA levels in AD and MCI" *Neurology*, (2001)56:A341-A342.

Mawal, Y., et al. "RT-PCR confirmation of suppressed HO-1 mRNA levels in Alzheimer lymphocytes" *Abstract to be presented at the 1st International Symposium on HO/CO*, Jul. 14-17, 2000.

McKhann, G., et al, "Clinical diagnosis of Alzheimer's disease: report of the NINCDS-ADRDA work group under the auspices of the Department of Health and Human Services Task Force on Alzheimer's Disease" *Neurology* Jul. 1984;34(7):939-944.

Morris, J., et al., "Very mild Alzheimer's disease: informant-based clinical assessment, neuropsychology, and pathological evaluation" *Neurology* Apr. 1991;41(4):469-478.

Murtha, S., et al., "Magnetic Resonance Imaging (MRI) Hippocampal Volumetric Shrinkage in Non-demented Memory-impaired Elderly" *Poster Presentation at the 4th Annual Rotman Research Institute Conference,* Toronto (1994).

Noonberg S.B., et al. "Detection of triplex-forming RNA oligonucleotides by triplex blotting" *Biotechniques* Jun. 1994;16(6):1070-1072, 1074.

Numazawa Satoshi, et al., "Cooperative induction of c-fos and heme oxygenase gene products under oxidative stress in human fibroblastic cells" *Experimental Cell Research*, (1997)237:434-444.

Premkumar, D., et al., "Induction of heme oxygenase-1 mRNA and protein neocortex and cerebral vessels in Alzheimer's disase" *J. Neurochem.*, (1995), 65:1399-1402.

Reichmann, H. and Reiderer, P. "Mitochondrial disturbances in neurodegeneration" In: Calne, D.B., (ed) *Neurodegenerative Diseases* (1994) Philadelphia, Saunders, pp. 195-204.

Rubin, E.H.,et al., "Very mild senile dementia of the Alzheimer type. I. Clinical assessment."*Archives Neurol.* Apr. 1989;46(4):379-382.

Sasaki, H., et al. "Improved method for the immobilization of heparin" *J. Chromatog.* (1987) 400:123-132.

Schagger, H., et al, *Soc. Neurosci Abstract,* 25th Annual Meeting, Nov. 11-16, 1995, p. 1492.

Schipper H.M., et al. "Evaluation of Heme Oxygenase-1 as a Systemic Biological Marker in AD" *Neurology* (2000) 54:1297-1304.

Schipper H.M., et al., "Expression of heme oxygenase-1 in the senscent and Alzheimer-diseased brain" *Ann. Neurol.* (1995) 37:758-768.

Schipper H.M., et al. "Mitochonrial iron sequestration in dopamine-challenged astroglia: role of heme oxygenase-1 and the permeability transition pore" *J. Neurochem.* (1999) 72:1802-1811.

Schipper H.M., et al., "Blood Heme Oxygenase Levels are decreased in Alzheimer's disease" *Proceedings of the 1997 Society for Neuroscience,* (1997)123:1-41.

Smith, M.A., et al., "Ultrastructural Localization of Heme Oxygenase-1 to the Neurofibrillary Pathology of Alzheimer's Disease", *Molecular and Chemical Neuropathy,* (1995)24:227-230.

Smith, Mark A., et al., "Heme Oxygenase-1 is Associated with the Neurofibrillary Pathology of Alzheimer's Disease", *American Journal of Pathology,* (1994)145:42-47.

Sopolsky, R.M. "Is this relevant to the human (ch. 14) in Sapolsky, R.M. (ed)" *Stress, the aging brain and the mechanisms of neuron death* (1992) The MIT Press, Cambridge, MA, pp. 305-339.

Spar, J., and Gerner, R., "Does the dexamethasone suppression test distinguish dementia from depression?" *Am. J. Psychiat.* Feb. 1982;139(2):238-40.

Suzuki Hidenori, et al., "Heme oxygenase-1 gene induction as an intrinsic regulation against delayed cerebral vasospasm in rats" *Journal of Clinical Investigation,* (1999)104:59-66.

Takahashi Kazuhiro, et al. "Suppression of heme oxygenase-1 mRNA expression by interferon-gamma in human glioblastoma cells" *Journal of Neurochemistry,*(1999)72:2356-2361.

Takahashi S., et al., "Positive and negative regulation of the human heme oxygenase-1 gene expression in cultured cells" *Biochimica et Biophysica ACTA.,* (1999)1447:231-235.

Wagner, S.L., et al., "Decreased levels of soluble amyloid beta-protein precursor are associated with Alzheimer's disease in concordant and discordant monozygous twin pairs." *Ann. Neurol.* Aug. 1994;36(2):215-220.

Wang, G.P., et al. *Acta Neuropathol.,* (1991), 82, pp. 6-12.

Yelton D.E. and Scharff M.D. "Monoclonal Antibodies: a powerful new tool in biology and medicine" *Ann. Rev. Biochem.* (1981) 50:657-680.

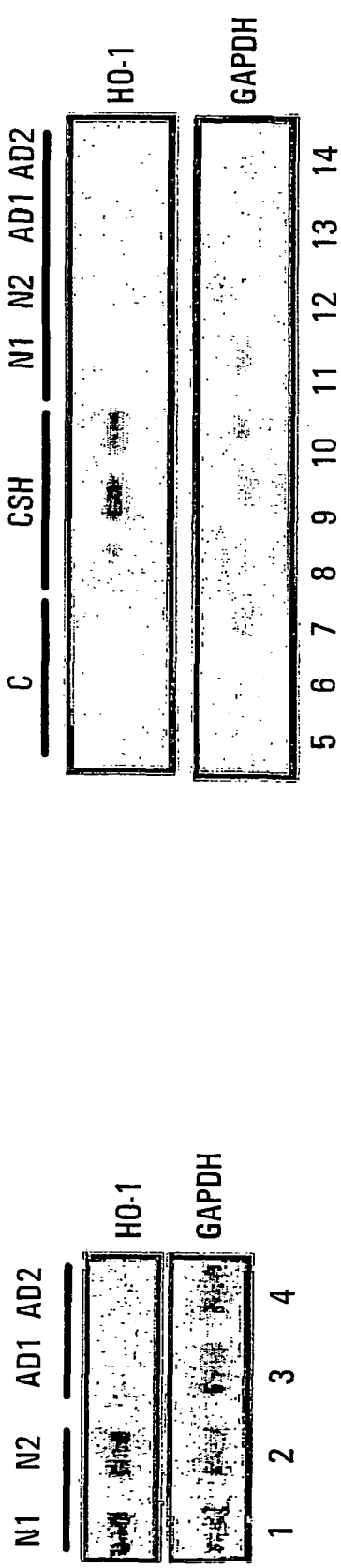
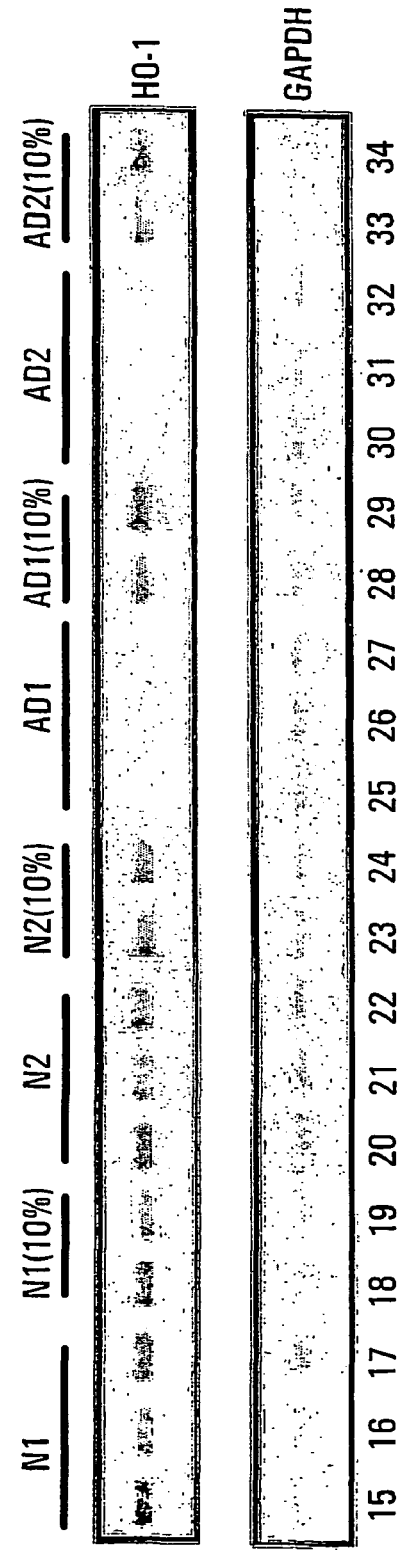
FIG. 1A
FIG. 1B
FIG. 1C

| PATIENT | DIAGNOSIS | HOS | AGE | MMSE | SEX | AD MEDS | ANTIOX. | CORTISOL |
|---|---|---|---|---|---|---|---|---|
| 295 | NYC | 0 | 42 | 30 | F | NONE | NONE | 215 |
| 296 | NYC | 0 | 56 | 28 | F | NONE | NONE | 163 |
| 297 | NYC | 0 | 25 | 30 | M | NONE | NONE | 234 |
| 298 | NYC | 0 | 35 | 30 | F | NONE | NONE | 183 |
| 299 | NYC | 0 | 40 | 30 | F | NONE | NONE | 121 |
| 300 | NYC | 0 | 47 | 30 | F | NONE | NONE | 245 |
| 301 | NYC | 0 | 39 | 30 | F | NONE | NONE | |
| 302 | NYC | 0 | 29 | 30 | F | NONE | NONE | |
| 319 | NEC | 0 | 67 | 28 | M | NONE | NONE | 176 |
| 325 | NEC | 0 | 66 | 29 | F | NONE | NONE | |
| 333 | NEC | 0 | 89 | 29 | M | NONE | NONE | 129 |
| 345 | NEC | 0 | 71 | 28 | F | NONE | NONE | 225 |
| 346 | NEC | 0 | 83 | 29 | M | NONE | NONE | 163 |
| 731 | NEC | 0 | 92 | 29 | F | NONE | NONE | |
| 335 | MCI | 2 | 79 | 29 | M | NONE | NONE | 270 |
| 337 | MCI | 0 | 56 | 30 | M | NONE | NONE | |
| 344 | MCI | 2 | 80 | 28 | M | NONE | NONE | |
| 351 | MCI | 0 | 79 | 28 | M | NONE | E800,C500 | 259 |
| 352 | MCI | 0 | 71 | 25 | F | NONE | NONE | |
| 354 | MCI | 0 | 72 | 29 | M | NONE | NONE | |
| 358 | MCI | 0 | 79 | 28 | M | NONE | E400,C500 | 289 |
| 472 | MCI | 3 | 82 | 27 | F | NONE | NONE | 312 |
| 293 | AD | 3 | 66 | 13 | F | ARICEPT | NONE | |
| 304 | AD | 3 | 70 | 26 | M | ARICEPT | NONE | |
| 305 | AD | 3 | 60 | 17 | M | ARICEPT | NONE | |
| 306 | AD | 3 | 83 | 19 | F | NONE | NONE | |
| 307 | AD | 3 | 68 | 21 | F | NONE | NONE | 292 |
| 310 | AD | 3 | 55 | 19 | F | ARICEPT | NONE | 136 |
| 312 | AD | 3 | 81 | 28 | M | NONE | NONE | 285 |
| 316 | AD | 3 | 78 | 28 | M | ARICEPT | NONE | 184 |
| 322 | AD | 2 | 68 | 13 | F | ARICEPT | NONE | |
| 328 | AD | 2 | 77 | 25 | M | ARICEPT | NONE | 69 |
| 330 | AD | 3 | 77 | 21 | M | NONE | NONE | 407 |
| 336 | AD | 3 | 81 | 23 | M | NONE | NONE | 278 |
| 342 | AD | 1 | 84 | 27 | F | NONE | NONE | |
| 343 | AD | 3 | 87 | 20 | F | ARICEPT | NONE | 187 |
| 347 | AD | 1 | 71 | 19 | F | ARICEPT | NONE | 265 |
| 355 | AD | 3 | 76 | 24 | M | ARICEPT | E400 | 135 |
| 356 | AD | 3 | 83 | 23 | F | NONE | NONE | 274 |
| 359 | AD | 3 | 66 | 21 | F | ARICEPT | E800 | 325 |
| 360 | AD | 3 | 82 | 20 | M | NONE | NONE | 311 |
| 475 | AD | 3 | 62 | 29 | M | ARICEPT | C500 | 292 |
| 714 | AD | 2 | 70 | 24 | F | NONE | NONE | |
| 730 | AD | 2 | 81 | 24 | M | NONE | NONE | |
| 294 | AD | 3 | 80 | 25 | M | ARICEPT | NONE | |

FIG. 2

HO-1 SUPPRESSOR AS A DIAGNOSTIC AND PROGNOSTIC TEST FOR DEMENTING DISEASES

This application claims the benefit of International Application No. PCT/CA1/01066, filed Jul. 25, 2001 and published on Jan. 31, 2002 as International Publication No WO 02/08449 A2 (incorporated herein by reference in its entirety), which claims the benefit of United States Provisional Application No. 60/220,813 filed on Jul. 25, 2000.

FIELD OF THE INVENTION

Applicant's related U.S. Pat. No. 6,210,895 (Apr. 3, 2001), herein incorporated by reference, relates to a method for predicting, diagnosing, and/or prognosticating dementing diseases such as Alzheimer Disease (AD) and Age-Associated Cognitive Decline (AACD). The invention relates to improved methods for predicting, diagnosing, prognosticating and/or treating dementing diseases such as Alzheimer Disease (AD) and Age-Associated Cognitive Decline (AACD) or Mild Cognitive Impairment (MCI) as well as methods and reagents to facilitate the study of the cause and progression of these diseases.

BACKGROUND OF THE INVENTION

Alzheimer Disease (AD) is a neurodegenerative disease which causes dementia. The terms "Alzheimer Disease" and "Alzheimer's Disease" are both utilized in the art, these terms being equivalent and are used interchangeably here and elsewhere. The period from first detection of AD to termination can range from a few years to 15 years, during which time the patient progressively suffers loss of both mental function and control of bodily functions. There is significant variability in the progress of the disease. While the majority of patients have a gradual, inexorable progression (losing on average 3 to 4 points on the 30 point Folstein mini-mental state score annually), approximately 30% of AD cases have a prolonged stable initial plateau phase lasting several years, as described in Haxby et al. (1992), herein incorporated by reference. A subgroup of patients has a fulminant, rapidly progressive downhill course over several years, as described in Mann et al. (1992), herein incorporated by reference. Other patients (about 10% of cohorts) remain slowly progressive, showing only gradual decline from year to year, as described in Grossi et al. (1988), herein incorporated by reference. The pathological, chemical and molecular bases of this heterogeneity remain undetermined. Recognition of the variability of AD progression represents an important clinical insight, and may explain the diagnostic difficulties presented by "atypical" cases.

Attempts at predicting the onset of AD or monitoring its progression have met with limited success. While in certain cases, there is a familial manifestation of the disease, it appears that the majority of AD cases are non-familial, and until recently (see below), no simple genetic marker for the disease had been determined. Much research has focused on the protein beta-amyloid, deposits of which are found in the brains of AD victims.

However, recently, as described in our related U.S. patent (U.S. Pat. No. 6,210,895 Apr. 3, 2001 and publication (Schipper et al., 2000), both herein incorporated by reference, we have devised a diagnostic method, useful in the prediction, diagnosis, and prognostication of AD, AACD/MCI, and related neurological diseases. This diagnostic method is based on the determination that patients suffering from AD have a significantly lower concentration of heme oxygenase-1 (HO-1) in their lymphocytes and plasma, and, accordingly, a significantly lower concentration of ribonucleotide sequences encoding HO-1 in their lymphocytes.

HO-1: Heme oxygenase-1 (HO-1) is an enzyme that catalyses the rapid degradation of heme to biliverdin in brain and other tissues. This 32 kDa member of the heat shock protein superfamily contains a heat-shock element in its promoter region and is rapidly up regulated in response to oxidative stress, metal ions, amino acid analogues, sulfhydryl agents, and hyperthermia. In response to oxidative stress, induction of HO-1 may result in protection of cells by catabolizing pro-oxidant metalloporphyrins, such as heme, into bile pigments (biliverdin, bilirubin), with free radical scavenging capabilities. Heme and other intracellular ferrous iron chelates are capable of converting hydrogen peroxide to the highly cytotoxic hydroxyl radical.

Using immunostaining techniques in conjunction with laser scanning confocal microscopy, intense HO-1 immunoreactivity in neurons and astrocytes of post-mortem hippocampus and temporal cortex derived from AD subjects has been observed, whereas neural HO-1 staining was faint or non-existent in the hippocampus and temporal cortex of control specimens matched for age and post-mortem interval, as noted in Schipper et al. (1995), herein incorporated by reference. Furthermore, consistent co-localization of HO-1 to neurofibrillary tangles and senile plaques in the AD specimens has been demonstrated. Finally, robust 32 kDa bands corresponding to HO-1 were observed by Western blotting of protein extracts derived from AD temporal cortex and hippocampus after SDS-PAGE, whereas control HO-1 bands were faint or absent. These results indicate that HO-1 is significantly over-expressed in neurons and astrocytes of AD hippocampus and cerebral cortex relative to control brains and support the contention that AD-affected tissues are experiencing chronic oxidative stress.

AACD/MCI: AACD and MCI are terms used to identify individuals who experience a cognitive decline that falls short of dementia. These terms are equivalent, MCI being a more recently adopted term, and are used interchangeably throughout this application. Satisfaction of criteria (World Health Organization) for this diagnosis requires a report by the individual or family of a decline in cognitive function, which is gradual, and present at least 6 months. There may be difficulties across any cognitive domains (although memory is impaired in the vast majority of cases), and these must be supported by abnormal performance on quantitative cognitive assessments for which age and education norms are available for relatively healthy individuals (i.e., the patient is compared to normal subjects his/her own age). Performance must be at least 1 SD below the mean value for the appropriate population on such tests. Neither dementia, nor significant depression or drug effects may be present. No cerebral or systemic disease or condition known to cause cerebral cognitive dysfunction may be present. In Applicant's experience, all patients who were classified as CDR.5 ("questionable dementia") on the Clinical Dementia rating scale and who met these exclusions, also met the criteria for AACD/MCI. About ⅓ of Alzheimer's patients have had a clearly definable period of isolated memory deficit which preceded their more global cognitive decline, as noted by Haxby et al. (1992), herein incorporated by reference. Using AACD/MCI criteria which look at other domains in addition to memory, the percentage with an identifiable prodrome is likely higher. Fortunately, not all AACD/MCI individuals seem to decline. It appears that a significant number of these subjects show a stable, non-progressive memory deficit on testing.

Related Disorders: Determining HO-1 concentration can also assist in predicting, diagnosing, or prognosticating other dementing diseases having similar manifestations and/or in distinguishing such diseases from AD. Such other diseases include Parkinson disease with dementia, Progressive Supranuclear Palsy, Vascular (i.e. multi-infarct) Dementia, Lewy Body Dementia, Huntington's Disease, Down's syndrome, normal pressure hydrocephalus, corticobasal ganglionic degeneration, multisystem atrophy, head trauma, neurosyphilis, Creutzfeld-Jacob disease and other prion diseases, HIV and other encephalitides, and metabolic disorders such as hypothyroidism and vitamin B12 deficiency. The method may also prove useful in differentiating the "pseudodementia" of depression from Alzheimer disease.

The determination of a relationship between HO-1 levels and AD represents a very significant advance in this field, and may be utilized for the development of methods of predicting, diagnosing in its very early stage, and prognosticating AD and other dementing diseases. However, identification of the factor(s) and mechanism(s) which control HO-1 expression in the normal versus the diseased state are needed, to provide even earlier diagnosis, as well as therapeutic methods and reagents or substances, and methods and reagents for the study of AD and other dementing diseases. In addition, the reduction or absence of HO-1 in patients suffering from AD represents a negative test, and, particularly for the purposes of diagnosis, it would be more desirable to have a positive indicator of disease, i.e. a factor whose presence (rather than absence) correlates with disease. Further, the decrease in HO-1 expression may represent an effect, rather than a cause of AD and other dementing diseases, therefore the identification of factor(s) and mechanism(s) which control HO-1 expression in the normal versus the diseased state are also needed to identify components and events which have an active causative role in the onset and progression of these diseases.

SUMMARY OF THE INVENTION

It is a goal of the present invention to provide improved methods for predicting, diagnosing, prognosticating and/or treating AD and other dementing diseases, as well as methods and reagents to facilitate the study of the cause and progression of these diseases.

Advantageously, embodiments of this invention provide an easily administered blood or cerebrospinal fluid test which is used to predict, diagnose, or prognosticate AD and other dementing diseases.

One aspect of the present invention is a heme oxygenase-1 suppressor (HOS) factor, wherein said factor attenuates the increase in the level of heme oxygenase-1 (HO-1). In an embodiment, such an increase occurs in response to exposure to an experimental agent or treatment which is capable of increasing the level of HO-1. For example, such experimental agents or treatments comprise exposure to any one or more of oxidative stress, metal ions, amino acid analogues, sulfhydryl agents (e.g., cysteamine, homocysteine), interleukin-1β, tumour necrosis factor-α (TNF-α) and hyperthermia.

Another aspect of the present invention is a method for assessing dementing diseases in a patient which comprises: determining the level of heme oxygenase-1 suppressor (HOS) factor or activity, in tissue or a body fluid obtained from a patient and comparing said level of HOS factor or activity with the corresponding level of HOS factor or activity in corresponding tissue or body fluid obtained from at least one control person, whereby if said level of HOS factor or activity is greater than said corresponding level of HOS factor or activity in said tissue or body fluid obtained from at least one control person then said patient suffers from a dementing disease wherein such method is used to predict the onset of, diagnose, or prognosticate dementing diseases.

Yet another aspect of the present invention is a diagnostic method for differentiating, in a patient suffering from a dementing disease, between a dementing disease which is HO-1-dependent and a dementing disease which is HO-1-independent, said method comprising: determining the level of heme oxygenase-1 suppressor (HOS) factor or activity, in tissue or a body fluid obtained from a patient suffering from a dementing disease and comparing said level of HOS factor or activity with the corresponding level of HOS factor or activity in corresponding tissue or body fluid obtained from at least one control person, whereby if said level of HOS factor or activity differs significantly from said corresponding level of HOS factor or activity in said tissue or body fluid obtained from at least one control person then said patient suffers from a dementing disease which is HO-1-dependent, and if said level of HOS factor or activity does not differ significantly from said corresponding level of HOS factor or activity in said tissue or body fluid obtained from at least one control person then said patient suffers from a dementing disease which is HO-1-independent.

In an embodiment, another aspect of the present invention is a method for differentiating the pseudodementia of depression from other dementing diseases in a patient which comprises: determining the level of heme oxygenase-1 suppressor (HOS) factor or activity, in tissue or body fluid obtained from a patient and comparing said level of HOS factor or activity with the corresponding level of HOS factor or activity in corresponding tissue or body fluid obtained from at least one control person whereby if said level of HOS factor or activity is greater than said corresponding level of HOS factor or activity in said corresponding tissue or body fluid obtained from at least one control person then said patient suffers from a dementing disease other than the pseudodementia of depression wherein such method is used to differentiate the pseudodementia of depression from other dementing diseases.

The dementing diseases assessed using the methods described above include, but are not limited to, Alzheimer Disease, Age-Associated Cognitive Decline, Mild Cognitive Impairment, Parkinson disease with dementia, Progressive Supranuclear Palsy, Vascular (i.e. multi-infarct) Dementia, Lewy Body Dementia, Huntington's Disease, Down's syndrome, normal pressure hydrocephalus, corticobasal ganglionic degeneration, multisystem atrophy, head trauma, neurosyphilis, Creutzfeld-Jacob disease and other prion diseases, HIV and other encephalitides, and metabolic disorders such as hypothyroidism and vitamin B12 deficiency. Further, as noted above, the methods may also prove useful in differentiating the "pseudodementia" of depression from Alzheimer disease.

Examples of the above mentioned tissue or body fluids include, but are not limited to, blood, plasma, lymphocytes, cerebrospinal fluid, urine, saliva, epithelia, and fibroblasts.

The above-mentioned control tissue or body fluid, for example, may be obtained from at least one normal age-matched control person or from the patient at another time, in an embodiment, at an earlier time.

Yet another aspect of the present invention is a method for assaying the level of heme oxygenase-1 (HO-1) suppressor (HOS) factor or activity in a sample which comprises: exposing the sample to a cell culture subjecting the cell culture to exposure to an experimental agent or treatment which may increase the level of HO-1 protein or mRNA encoding HO-1; determining the level of HO-1 protein or mRNA encoding HO-1; and comparing said level of HO-1 protein or mRNA encoding HO-1 with a corresponding control level of HO-1 protein or mRNA encoding HO-1;

whereby the level of said HO-1 protein or mRNA encoding HO-1 inversely correlates with the level of HOS factor or activity.

The present invention also provides evidence for the existence of a putative heme oxygenase-1 (HO-1) suppressor (HOS) factor in the samples derived from a patient suffering a dementing disease, as well as a partially purified fraction comprising HOS activity and a corresponding putative HOS factor.

Accordingly, a further aspect of the present invention is a method for assaying the level of heme oxygenase-1 (HO-1) suppressor (HOS) factor or activity in a sample which comprises: exposing the sample to a cell culture subjecting the cell culture to exposure to an experimental agent or treatment which may increase the level of HO-1 protein or mRNA encoding HO-1; determining the level of HO-1 protein or mRNA encoding HO-1; and comparing said level of HO-1 protein or mRNA encoding HO-1 with a corresponding control level of HO-1 protein or mRNA encoding HO-1; whereby the level of said HO-1 protein or mRNA encoding HO-1 inversely correlates with the level of HOS factor or activity.

The above-mentioned corresponding control level of HO-1 protein or mRNA may be obtained, for example, by assaying the level of HO-1 protein or mRNA in a corresponding cell culture which has been subjected to exposure to the above-mentioned experimental agent or treatment, but has not been exposed to the above-mentioned sample prior to exposure to the above-mentioned experimental agent or treatment.

Additional aspects of the present invention are polyclonal and monoclonal antibodies which recognize the HOS factor, as well as hybridoma cells which produce the latter monoclonal antibodies.

Yet a further aspect of the present invention is a method for assaying the level of heme oxygenase-1 (HO-1) suppressor (HOS) factor or activity in a sample comprising: exposing said sample to an antibody which recognizes the HOS factor; isolating immune complexes; and determining the level of HOS factor or activity in the immune complex.

Since HOS affects the levels of HO-1 mRNA and protein, therefore the invention also contemplates a method for assaying the level of HOS activity or factor using a reporter construct comprising transcriptional regulatory element(s) (e.g., a promoter region) of the HO-1 gene operably linked to a suitable reporter gene.

Accordingly, a further aspect of the present invention is a method for assaying the level of heme oxygenase-1 (HO-1) suppressor (HOS) activity in a sample comprising: exposing said sample to a reporter construct, wherein said reporter construct comprises the HO-1 promoter region and a reporter gene, wherein said reporter gene encodes a protein which possesses a detectable reporter activity; determining the level of said reporter activity, and comparing said level of said reporter activity with a corresponding control level of said reporter activity; whereby the level of said reporter activity inversely correlates with the level of HOS factor or activity.

The above-mentioned control level of reporter activity may be obtained, for example, by measuring the reporter activity produced by a corresponding reporter construct that has not been exposed to the above-mentioned sample.

The HOS activity of the present invention may also be used for the elucidation of other factors and mechanisms involved in the onset and progression of AD and other dementing diseases. These factors and mechanisms may yield therapeutic agents and methods, as well as contribute to our understanding of the molecular events which are involved in the onset and progression of AD and other dementing diseases.

Therefore, a further aspect of the present invention is a method for screening a candidate compound for the presence of an inhibitor or activator of HOS activity or HOS factor comprising: exposing said candidate compound to a sample known to comprise HOS activity or HOS factor; assaying the level of HOS activity or HOS factor using a method selected from the group consisting of: (a) a method for assaying the level of heme oxygenase-1 (HO-1) suppressor (HOS) factor or activity in a sample which comprises: exposing the sample to a cell culture; subjecting the cell culture to exposure to an experimental agent or treatment which may increase the level of mRNA encoding HO-1; determining the level of HO-1 protein or mRNA encoding HO-1; and comparing said level of HO-1 protein or mRNA encoding HO-1 with a corresponding control level of HO-1 protein or mRNA encoding HO-1; whereby the level of said HO-1 protein or mRNA encoding HO-1 inversely correlates with the level of HOS factor or activity; (b) a method for assaying the level of heme oxygenase-1 (HO-1) suppressor (HOS) factor or activity in a sample comprising: exposing said sample to an antibody which recognizes the HOS factor; isolating immune complexes and determining the level of HOS factor or activity in the immune complex; and (c) a method for assaying the level of heme oxygenase-1 (HO-1) suppressor (HOS) factor or activity in a sample comprising: exposing said sample to a reporter construct, wherein said reporter construct comprises the HO-1 promoter region and a reporter gene, wherein said reporter gene encodes a protein which possesses a detectable reporter activity and determining the level of said reporter activity; and comparing said level of said reporter activity; with a corresponding control level of said reporter activity; whereby the level of said reporter activity inversely correlates with the level of HOS factor or activity and comparing said level of HOS activity or HOS factor with a corresponding control level of HOS activity or HOS factor in a corresponding control sample, wherein said control sample comprises said sample known to comprise HOS activity that has not been exposed to said candidate compound.

A further aspect of the present invention is a commercial package comprising means for determining the level of heme oxygenase-1 (HO-1) suppressor (HOS) factor or activity, in tissue or body fluid obtained from a patient, and instructions for comparing said level of HOS factor or activity with an established standard of the corresponding HOS activity in corresponding control tissue or body fluid. Such control tissue or body fluid, for example, may be obtained from at least one normal age-matched control person or from the patient at another time, in an embodiment, at an earlier time.

Since levels of HO-1 mRNA, protein and/or activity as well as HOS factor and/or activity may be altered in patients suffering from a dementing disease, inhibitors or activators of HOS factor or HOS activity represent potential substances or compounds which may be utilized for the treatment of a dementing disease.

Accordingly, a further aspect of the present invention is a compound for the treatment of a dementing disease, wherein the compound alleviates the dementing disease by increasing or decreasing the level of heme oxygenase-1 (HO-1) mRNA, protein or activity.

A further aspect of the present invention is a compound for the treatment of a dementing disease, wherein the compound alleviates the dementing disease by increasing or decreasing the level of heme oxygenase-1 (HO-1) suppressor (HOS) factor or activity.

Yet a further aspect of the present invention is a pharmaceutical composition for the treatment of a dementing disease which comprises the substance or compound described above in admixture with a suitable pharmaceutically acceptable diluent or carrier.

Yet a further aspect of the present invention is a method of treating a dementing disease in a patient, comprising administering to said patient the compound or pharmaceutical composition described above in an amount effective to treat a dementing disease, wherein said method results in the alleviation of the dementing disease by increasing or decreasing the level of heme oxygenase-1 (HO-1) mRNA, protein or activity.

Yet a further aspect of the present invention is a method of treating a dementing disease in a patient, comprising administering to said patient the compound or pharmaceutical composition described above in an amount effective to treat a dementing disease, wherein said method results in the alleviation of the dementing disease by increasing or decreasing the level of heme oxygenase-1 (HO-1) suppressor (HOS) factor or activity.

Yet a further aspect of the present invention is a use of the above-mentioned compound or pharmaceutical composition for the treatment of a dementing disease.

Yet a further aspect of the present invention is a commercial package containing as an active pharmaceutical ingredient the compound or pharmaceutical composition described above together with instructions for its use in the treatment of a dementing disease.

The substance or compound, composition, method and commercial package noted above may, for example, be utilized for the treatment of a dementing disease selected from the group consisting of Alzheimer Disease, Age-Associated Cognitive Decline, Mild Cognitive Impairment, Parkinson disease with dementia, Progressive Supranuclear Palsy, Vascular (i.e. multi-infarct) Dementia, Lewy Body Dementia, Huntington's Disease, Down's syndrome, normal pressure hydrocephalus, corticobasal ganglionic degeneration, multisystem atrophy, head trauma, neurosyphilis, Creutzfeld-Jacob disease and other prion diseases, HIV and other encephalitides, and metabolic disorders such as hypothyroidism and vitamin B12 deficiency.

BRIEF DESCRIPTION OF THE DRAWINGS

FIGS. 1A–1C Northern analysis of HO-1 mRNA implicating the presence of a circulating HO-1 suppressor (HOS) factor in sporadic AD, as described in Example 1. Control GAPDH bands used to ensure uniformity of RNA loading are depicted below the HO-1 bands.

FIG. 2 depicts tabular results of studies of demographics and HOS activity in normal young control (NYC), normal elderly control (NEC), mild cognitive impairment (MCI) and sporadic Alzheimer disease (AD) subjects, as described in Example 2. Suppression by 24 h incubation in human plasma of CSH-induced (880 μM×6 h) glial HO-1 mRNA band (Northern blot) relative to CSH-treated astrocytes grown in standard culture media; 0=0–25% suppression, 1=26–50% suppression, 2=51–75% suppression, 3=76–100% suppression. HOS=HOS activity MMSE=Folstein Mini-mental State Exam Score; Cortisol=Plasma cortisol levels (nMol/L); AD Meds=cholinesterase inhibitors used for treatment of Alzheimer disease; E400 and E800=400 and 800 units vitamin E, respectively; C500=500 mg vitamin C.

DESCRIPTION OF THE EMBODIMENTS OF THE INVENTION

Figure 3:
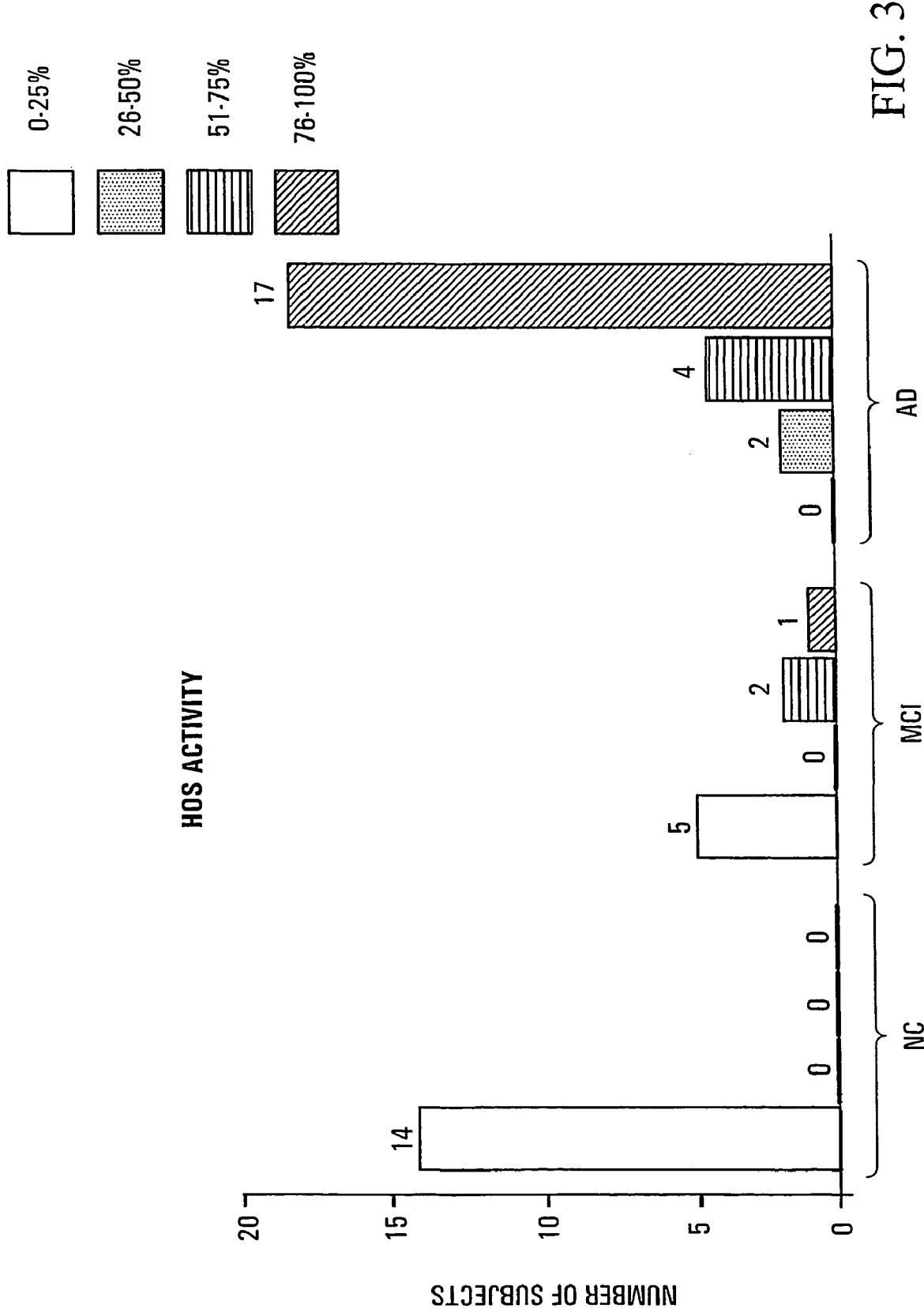
FIG. 3 depicts graphical results of HOS activity in normal control (NC), mild cognitive impairment (MCI) and sporadic Alzheimer disease (AD) subjects. HOS activity=percentage suppression (quartiles) by 24 h incubation in human plasma of CSH-induced (880 μM×6 h) glial HO-1 mRNA band (Northern blot) relative to CSH-treated astrocytes grown in standard culture media, as described in Example 3.

Applicant has devised an improved diagnostic method, useful in the prediction, diagnosis, and prognostication of AD, AACD/MCI, and related neurological diseases, as well as methods and reagents which are useful in the treatment and study of AD, AACD/MCI, and related neurological diseases. These methods are based on the discovery that patients suffering from AD have an activity and corresponding factor in their plasma which significantly suppresses the expression of heme oxygenase-1 (HO-1). This HO-1 suppressor activity is assayed via the inability to upregulate the concentration of nucleotide sequences encoding HO-1, in response to exposure to a suitable experimental agent or treatment, in a suitable cell culture system pre-incubated with a tissue or body fluid derived from patients suffering from AD or other dementing diseases. This suppressor activity and corresponding factor shall be referred to as HO-1 suppressor (HOS) activity and factor, respectively.

Applicant has identified an activity, namely HOS activity, which is present in tissue or body fluids derived from patients suffering from AD as well as possibly those suffering from other dementing diseases, but is absent in normal age-matched control subjects. This activity may be detected in a tissue or body fluid obtained from these patients. Examples of possible sources of suitable tissue or body fluids include blood, plasma, lymphocytes, cerebrospinal fluid, urine, saliva, epithelia (such as skin epithelia) and fibroblast cell lines derived from patients.

An aspect of the invention is a HOS activity, which is an activity that suppresses the upregulation of HO-1 expression. Such upregulation occurs, for example, following exposure to an experimental agent or treatment which is, in the absence of HOS activity, capable of increasing HO-1 expression, as detected by increases in HO-1 protein or HO-1 mRNA. In patients suffering from AD, as well as possibly those suffering from other dementing diseases, HOS activity suppresses the expression of HO-1, which is expressed at significantly higher levels in lymphocytes and possibly other non-neural tissue or body fluids in normal aged-matched control subjects.

A further aspect of the invention is a method of assaying HOS activity in a sample. Examples of possible sources of suitable samples include tissues and body fluids such as, for example, blood, plasma, lymphocytes, cerebrospinal fluid, urine, saliva, epithelia and fibroblast cell lines derived from patients, or fractions derived from these samples. The assay involves exposing the sample to be tested to a cell culture that is capable of undergoing an induction in HO-1 expression in response to exposure to a certain experimental agent or treatment. An example of such a cell culture is a rat astroglial culture, however, many other useful possibilities exist. Examples of such exposure to an experimental agent or treatment include exposure to oxidative stress, metal ions, amino acid analogues, sulfhydryl agents, interleukin-1β, tumour necrosis factor-α (TNF-α) and hyperthermia. Examples of suitable sulfhydryl reagents include, but are not limited to, cysteamine and homocysteine. Following such exposure to an experimental agent or treatment, the level of HO-1 protein or HO-1 mRNA may be detected using suitable methods. The level of HO-1 may for example be detected by an immunoassay. The level of HO-1 mRNA may for example be detected by Northern analysis using an appropriate probe(s). Detection of HO-1 mRNA of greater sensitivity may be achieved for example using the reverse transcriptase-polymerase chain reaction (RT-PCR) method, described in Abraham (1998) and Mawal et al. (2000), both herein incorporated by reference. The activity assay may be adapted to a large scale level for analyzing a large number of samples simultaneously, possibly in a suitable array format, possibly with the automated execution (e.g., by robotics) of some or all of the steps therein.

A further possibility may be the development of a reporter-based assay for assaying HOS activity. Such an assay may involve the preparation of a suitable reporter construct, e.g. comprising a transcriptional regulatory element, such as the 5' untranslated promoter region, of the HO-1 gene, operably linked to a suitable reporter gene, i.e., capable of regulating the expression of a suitable reporter gene. Such a construct may additionally comprise the 3' untranslated region of the HO-1 gene or another suitable 3' sequence. In another embodiment, the construct may comprise an in frame fusion of a suitable reporter gene within the open reading frame of the HO-1 gene. The reporter gene may be chosen as such to facilitate the detection of its expression, e.g. by the detection of the presence and/or activity of its gene product. Many such suitable reporters may be used, which provide detectable signals. Most preferred embodiments in this class are those that provide a conveniently detectable signal, which may be detected by, for example, spectroscopic methods. Examples of suitable reporter genes include those encoding luciferase, beta-galactosidase, green fluorescent protein, alkaline phosphatase, chloramphenicol acetyltransferase, as well as others. Such a reporter construct may be introduced into a suitable system capable of exhibiting an increase in the level of expression of the reporter gene in response to exposure to an experimental agent or treatment which is capable of increasing HO-1 expression as noted above. Such an assay would also be adaptable to a possible large scale, high-throughput, automated format as noted above, and would allow more convenient detection due to the presence of its reporter component.

Using methods of assaying HOS activity as described above, applicant has determined that the level of HOS activity in a sample decreases with the increasing dilution of the sample, suggesting that HOS activity is attributed to the presence of a corresponding HOS factor. Using the same assay methods, applicant has further determined that preheating the sample to be tested abrogates HOS activity, suggesting that HOS activity is attributed to a protein or complex of proteins. Since, to applicant's knowledge, glucocorticoids are the only known suppressors of HO-1 expression (Lavrovsky et al., 1996; Deramaudt et al., 1999), the discovery of a protein-like HOS factor is novel. Applicant has further demonstrated that cortisol levels are not increased in AD or MCI samples with respect to normal samples, thus demonstrating that suppression of HO-1 expression in AD and MCI samples is not attributed to glucocorticoids, but rather, is a result of the activity of a (non-glucocorticoid) HOS factor.

Applicant has accomplished a partial purification of HOS activity and therefore HOS factor using one or multiple chromatographic methods in sequential fashion. An example of a suitable chromatographic method is affinity chromatography using a heparin-agarose matrix or a concanavalin-A (Con-A) agarose matrix or gel filtration chromatography using for example a Superose™-12 matrix. Applicant has accomplished further purification of HOS factor using heparin-agarose, concanavalin-A (Con-A) agarose and Superose™-12 chromatography, in sequence, further suggesting that HOS factor comprises a protein or complex of proteins, and, based on binding to the Con-A matrix, likely comprises a glycoprotein, in an embodiment, a mannoprotein. This suggests that HOS activity and the corresponding HOS factor may be obtained in a more highly purified form using various chromatographic methods. Such purification is for example shown in FIG. 11, where the peak of HOS activity elutes later that most of the protein in the sample, thus indicating that the Superose™-12 column has removed the majority of protein contaminants from the HOS factor-containing sample. Calibration of the column using known protein molecular weight standards (FIG. 12) indicates that HOS factor is a protein or complex of proteins having an approximate molecular weight in the range of 80–100 kDa, in an embodiment, having a molecular weight of approximately 90 kDa. These data thus provide further support that HOS factor is a protein-like molecule. Applicant has further shown that HOS factor and associated HOS activity are stable during prolonged storage.

Accordingly, the invention further provides a HOS factor, as described above.

Applicant has further demonstrated that HOS activity is not due to simple antioxidant behavior, since both AD and normal plasma exhibit equivalent levels of partial suppression of the HO-1 mRNA response to a pro-oxidant, for example, menadione. Further, typical doses of antioxidants have no effect on the induction of HO-1 mRNA expression, and exposure of multiple, high dose, antioxidants only results in partial suppression.

A further aspect of the present invention is an improved diagnostic method, potentially useful in the prediction, diagnosis, and prognostication of AD, AACD/MCI, and related neurological diseases. This diagnostic method is based on the detection of HOS activity, using for example the assay methods described above, in a tissue or body fluid obtained from a patient. Because the presence of HOS activity precedes any decrease in HO-1 expression in a patient, this diagnostic method provides an even earlier diagnosis of AD, AACD/MCI, and related neurological diseases. In addition, the immunodetection of HOS factor or activity (see below) may provide an improved method of diagnosis over the detection of decreases in HO-1 expression using methods such as Northern analysis or the reverse transcriptase-polymerase chain reaction (RT-PCR) method, described in Abraham (1998) and Mawal et al. (2000), both herein incorporated by reference. Further, the correlation of the presence of HOS activity with the disease state represents a positive test for diagnosis. This is more desirable than a negative test, used for diagnosis based on the reduction or absence of HO-1 expression in a patient suffering from one of the dementing diseases described above.

It is known in the art that certain dementing diseases, for example, AD, correlate with changes in HO-1 levels while others do not. Such dementing diseases may be categorized as HO-1-dependent and HO-1-independent. As described in the instant application, such changes in HO-1 levels are a result of changes in the levels of HOS factor or activity. Therefore, the invention further relates to methods, reagents, compounds and commercial packages to differentiate a dementing disease which exhibits a significantly altered level of HO-1 protein, HO-1 mRNA, HOS factor, or HOS activity, i.e., an HO-1-dependent dementing disease, from a dementing disease which does not exhibit such a significantly altered level of HO-1 protein, HO-1 mRNA, HOS factor, or HOS activity, i.e., an HO-1-independent dementing disease. The term "significantly" as used here means that the levels are altered from control levels beyond the range of experimental error, as known in the art.

The HOS activity of the present invention may also be used to develop therapeutic agents and methods for the treatment of AD and other dementing diseases. Since the appearance of HOS activity correlates with the presence of the disease state, the HOS activity and HOS factor is expected to play a causative role in the onset and/or progression of AD and other dementing diseases. Therefore, identification of factors or mechanisms which inhibit or activate HOS activity may be utilized for the development of therapeutic agents and methods for the treatment of AD and other dementing diseases. If an increase in HOS activity is a causative event in the onset and/or progression of AD and other dementing diseases, an inhibitor of HOS activity is expected to have therapeutic potential. Conversely, an activator of HOS activity is expected to represent an upstream causative agent of the onset and/or progression of AD and other dementing diseases, which may provide even earlier and improved methods of diagnosis. Further, all factors which effect HOS activity will lead to a better understanding of the mechanisms of the onset and/or progression of AD and other dementing diseases, and ultimately contribute to the development of improved therapeutic methods and agents. In addition, other factors which affect levels of HO-1 mRNA, protein and activity are also useful to the invention, similar to the above, and are thus a further aspect of the invention.

Accordingly, it is a further aspect of the present invention to provide a HOS activity-based screening method to identify putative compounds which either inhibit or augment HOS activity. Such screening may be performed using for example the HOS activity assays described above, and may be adapted to a large scale, and possibly automated format. Such a method may comprise exposing a known HOS activity-containing sample to the compound to be tested, and subsequently determining the level of HOS activity present, which is then compared to a control sample that was not exposed to the compound to be tested. In a high-throughput, automated format, this screening method may be used for the rapid analysis of libraries containing a large number of compounds for their effects on HOS activity. In an embodiment, examples of such libraries include chemical libraries prepared by combinatorial synthesis.

The partially purified fraction comprising HOS factor and HOS activity, obtained, for example, from heparin-agarose and/or Con-A agarose and/or Superose™-12 column chromatography, may be used to immunize a small mammal, e.g., a mouse or a rabbit, in order to raise antibodies which recognize this activity. In an embodiment the above mentioned fraction is obtained from sequential heparin-agarose, Con-A agarose and Superose™-12 column chromatography. Accordingly, a further aspect of the invention provides an antibody that recognizes the HOS factor of the invention.

An antibody of the invention is either polyclonal or monoclonal. Antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monoclonal antibodies may also be in the form of immunoglobulin fragments, e.g., F(ab)'$_2$, Fab or Fab' fragments. The antibodies of the invention are of any isotype, e.g., IgG or IgA, and polyclonal antibodies are of a single isotype or a mixture of isotypes.

Antibodies against the HOS factor of the present invention are generated by immunization of a mammal with a partially purified fraction comprising HOS factor. In an embodiment the above mentioned fraction is obtained from sequential heparin-agarose, Con-A agarose and Superose™-12 column chromatography. Such antibodies may be polyclonal or monoclonal. Methods to produce polyclonal or monoclonal antibodies are well known in the art. For a review, see Harlow and Lane (1988) and Yelton et al. (1981), both of which are herein incorporated by reference. For monoclonal antibodies, see Kohler and Milstein (1975), herein incorporated by reference.

The antibodies of the invention, which are raised to a partially purified fraction comprising HOS factor of the invention, are produced and identified using standard immunological assays, e.g., Western blot analysis, dot blot assay, or ELISA (see, e.g., Coligan et al. (1994), herein incorporated by reference). The antibodies are used in diagnostic methods to detect the presence of a HOS factor and activity in a sample, such as a tissue or body fluid. The antibodies are also used in affinity chromatography for obtaining a purified fraction comprising the HOS factor and activity of the invention.

Accordingly, a further aspect of the invention provides (i) a reagent for detecting the presence of HOS factor and activity in a tissue or body fluid; and (ii) a diagnostic method for detecting the presence of HOS factor and activity in a tissue or body fluid, by contacting the tissue or body fluid with an antibody of the invention, such that an immune complex is formed, and by detecting such complex to indicate the presence of HOS factor and activity in the sample or the organism from which the sample is derived.

Those skilled in the art will readily understand that the immune complex is formed between a component of the sample and the antibody, and that any unbound material is removed prior to detecting the complex. It is understood that an antibody of the invention is used for screening a sample, such as, for example, blood, plasma, lymphocytes, cerebrospinal fluid, urine, saliva, epithelia and fibroblasts, for the presence of HOS activity.

For diagnostic applications, the reagent (i.e., the antibody of the invention) is either in a free state or immobilized on a solid support, such as a tube, a bead, or any other conventional support used in the field. Immobilization is achieved using direct or indirect means. Direct means include passive adsorption (non-covalent binding) or covalent binding between the support and the reagent. By "indirect means" is meant that an anti-reagent compound that interacts with a reagent is first attached to the solid support. Indirect means may also employ a ligand-receptor system, for example, where a molecule such as a vitamin is grafted onto the reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent is labeled with a detection means which allows for the detection of the reagent when it is bound to its target. The detection means may be a fluorescent agent such as fluorescein isocyanate or fluorescein isothiocyanate, or an enzyme such as horse radish peroxidase or luciferase or alkaline phosphatase, or a radioactive element such as $^{125}$I or $^{51}$Cr.

Accordingly, a further aspect of the invention provides a process for purifying, from a tissue or body fluid, the HOS factor of the invention, which involves carrying out antibody-based affinity chromatography with the tissue or body fluid, wherein the antibody is an antibody of the invention.

For use in a purification process of the invention, the antibody is either polyclonal or monoclonal, and preferably is of the IgG type. Purified IgGs are prepared from an antiserum using standard methods (see, e.g., Coligan et al. (1994), herein incorporated by reference). Conventional chromatography supports, as well as standard methods for grafting antibodies, are described in, e.g., Harlow and Lane (1988), herein incorporated by reference, and outlined below.

Briefly, a tissue or body fluid, such as plasma from a patient suffering from AD, preferably in a buffer solution, is applied to a chromatography material, preferably equilibrated with the buffer used to dilute the tissue or body fluid so that the HOS factor of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3 M MgCl$_2$). Eluted fractions are recovered and the presence of the antigen is detected, e.g., by measuring the absorbance at 280 nm.

A further aspect of the present invention is a diagnostic imaging method, which comprises introducing into a biological system, an antibody of the invention, which is used in conjunction with an appropriate detection system to identify areas where HOS factor or activity is present or absent.

The following examples are provided in order to illustrate the methods of the present invention and are not meant to limit the scope of the invention.

EXAMPLE 1

Determination of the Presence of HOS Activity in Plasma Derived from AD Patients Whole blood is collected from normal elderly (N1, N2) subjects or patients with probable sporadic AD (AD1, AD2) in heparinized tubes. This is then layered over a Ficoll Paque™ density gradient and centrifuged at 1800 rpm for 20 minutes. The top plasma layer is then collected and saved for incubation with rat astroglia as described below. The lymphocyte fractions are collected and used for the isolation of mRNA for Northern analysis as described below.

Determination of lymphocyte HO-1 mRNA levels: Lymphocyte fractions were obtained by differential centrifugation of whole blood on Ficoll Paque™ gradients as described above. Cytoplasmic RNA was isolated from the lymphocytes using an acid guanidinium thiocyanate-phenol-chloroform extraction method, as described by Chomczynski et al. (1997), Biotechniques 22(3):550–3, herein incorporated by reference. Six micrograms of RNA was denatured and size-separated by electrophoresis on 1% agarose/formaldehyde gels. RNA integrity was confirmed by ethidium bromide staining. The RNA was transferred onto Hybond-N™ filter paper and covalently cross-linked to the membrane by UV light for two minutes. The hybridization probe (HO-1; 1.0 kb) was prepared by random priming using the Random Primer DNA Labeling System, as described by Feinberg et al. (1984), herein incorporated by reference. Prehybridization was performed for 12 hours at 42° C. in a buffer containing formamide deionized, 5× Denhardt's reagent, 6×SSPE and 0.5% SDS. The hybridization buffer consisted of the prehybridization buffer without 5× Denhardt's reagent, and $^{32}$P-labelled denatured DNA probe, as described in Noonberg et al. (1994), herein incorporated by reference. Equal loading of RNA was confirmed by hybridization with a cDNA for the (housekeeping) gene, glyceraldehyde-3-phosphate dehydrogenase (GAPDH). All washes were performed under stringent conditions (1×SSC and 0.2% SDS for 45 minutes at room temperature, 0.4×SSC and 0.2% SDS for 15 minutes at 65 C). The RNA hybridizing with cDNA probes was visualized by autoradiography using an intensifying screen at −80 C, as described in Church et al. (1984), herein incorporated by reference.

As noted in our related U.S. patent (U.S. Pat. No. 6,210,895; Apr. 13, 2001) and publication (Schipper et al., 2000), both herein incorporated by reference, and as reiterated in Panel A of FIG. 1, lymphocytes isolated from normal subjects N1 and N2 exhibit significant levels of HO-1 mRNA (lanes 1 and 2), which is not detectable in lymphocytes isolated from AD patients AD1 and AD2 (lanes 3 and 4).

Assay of Plasma HOS Activity Via the Induction of HO-1 Expression Upon Cysteamine (CSH) Treatment of Rat Astroglia Brain cell cultures: Rat astroglia were prepared as described in Schipper et al. (1999), herein incorporated by reference, as follows:

Pregnant Sprague-Dawley rats were obtained from Charles River Breeding Farms. Primary neural cell cultures were prepared from 1-day old neonates by mechanoenzymatic dissociation of cerebral tissue or body fluid as previously described by Chopra et al., (1997), herein incorporated by reference. Cells were grown in Ham's F-12 and high-glucose DMEM (50:50 vol/vol) supplemented with 10 mM HEPES, 5% heat-inactivated horse serum, 5% heat-inactivated fetal bovine serum, and penicillin/streptomycin (50 U/ml and 50 µg/ml, respectively). The cells were plated in 75-cm$^2$ tissue or body fluid culture flasks at a density of 1×10$^6$ cells/ml. Cultures were incubated at 37 C in humidified 95% air/5% CO$_2$ for 6 h, at which time they were vigorously shaken 20–30 times with replacement of fresh medium to remove adherent oligodendroglia and microglia from the astrocytic monolayers. The cultures were then incubated under the above-mentioned conditions for 6 days, at which time >98% of the cells composing the monolayer were astroglia, as determined by immunohistochemical labeling for the astrocyte-specific marker glial fibrillary acidic protein, as described by Chopra et al. (1995), herein incorporated by reference. These astroglia cultures were grown under different conditions and subjected to different treatments (see below), and subsequently mRNA was isolated for Northern analysis of HO-1 mRNA levels as described in Schipper et al. (1999), herein incorporated by reference, as follows:

RNA isolation and Northern analysis: Cultured astrocytes were harvested using a rubber policeman, and cytoplasmic RNA was isolated using an acid guanidinium thiocyanate/phenol/chloroform extraction method, as described by Chomczynski and Sacchi (1987), herein incorporated by reference. Ten micrograms of RNA was denatured and size-separated by electrophoresis on 1% agarose/formaldehyde gels. RNA integrity was confirmed by ethidium bromide staining. The RNA was transferred onto Hybond-N™ filter paper and covalently cross-linked to the membrane by UV light for 2 min. The hybridization probe (HO-1; 1.0 kb) was prepared by random primer-generated double-strand DNA probes using the random primer DNA labeling system, as described by Feinberg and Vogelstein (1984), herein incorporated by reference. Prehybridization was performed for 12 h at 42 C in a buffer containing formamide-deionized, 5× Denhardt's reagent, 6× saline-sodium phosphate-EDTA, and 0.5% sodium dodecyl sulfate (SDS). The hybridization buffer consisted of the prehybridization buffer without 5× Denhardt's reagent and $^{32}$P-labeled denatured DNA probe, as described by Noonberg et al. (1994), herein incorporated by reference. Equal loading of RNA was confirmed by hybridization with a cDNA for the (housekeeping) gene, glyceraldehyde-3-phosphate dehydrogenase (GAPDH), or 18S mRNA. All washes were performed under stringent conditions [1×saline-sodium citrate (SSC) and 0.2% SDS for 45 min at room temperature, 0.4×SSC and 0.2% SDS for 15 min at 65 C, and 0.1×SSC and 0.2% SDS for 15 min at 65° C.]. The RNA hybridizing with cDNA probes was SDS for 15 min at 65 C, and 0.1×SSC and 0.2% SDS for 15 min at 65 C]. The RNA hybridizing with cDNA probes was visualized by autoradiography using an intensifying screen at −80 C, as described by Church and Gilbert (1984), herein incorporated by reference. Resulting bands on the autoradiograph were analyzed using a phosphorimager S1 densitometer. Densitometry data were normalized by calculating the ratios of the HO-1 mRNA signals to control GAPDH or 18S mRNA signals.

FIG. 1, panel A: Northern blot of lymphocyte HO-1 mRNA (and control GAPDH mRNA) derived from 2 normal elderly individuals (N1, N2) and 2 patients with probable sporadic AD AD1, AD2). As noted in our related U.S. Patent (U.S. Pat. No. 6,210,895; Apr. 13, 2001 and publication (Schipper et al., 2000), both herein incorporated by reference, lymphocyte HO-1 mRNA bands are visible in the controls (lanes 1 and 2), and not detectable (lanes 3 and 4) in the AD subjects, indicating the presence of HOS activity in the latter.

Using the methods described above, Northern analysis of HO-1 mRNA levels of rat astroglia grown under different conditions and subjected to different treatments was performed, the results of which are shown in panels B and C of FIG. 1. Panel B: Control (unchallenged) rat astroglia grown in standard culture media for 6 days exhibit faint or no HO-1 mRNA bands (lanes 5–7). Cysteamine (CSH) treatment (880 µM×6 hr) induces robust HO-1 mRNA bands in these cells (lanes 8–10). Twenty-four hour incubation of the rat astroglia with the plasma derived from the same 2 normal subjects (N1, N2; lanes 11–12) and the 2 AD patients (AD1, AD2lanes 13–14) noted above (see panel A) has no appreciable affect on baseline HO-1 mRNA levels. Panel C: In contrast to plasma derived from the 2 normal subjects (lanes 15–24), undiluted plasma from the 2 AD patients markedly suppresses the rat astroglial HO-1 mRNA response to CSH (lanes 25–27; 30–32). Dilution of the AD plasma (1:9 in standard culture media; "10%") greatly diminishes its inhibitory effect on CSH-induced HO-1 mRNA expression (lanes 28–29; 33–34). Therefore, there exists in the plasma of AD patients an HOS activity, which is not present in the plasma of normal subjects, and which is assayable by the determination of HO-1 mRNA levels in rat astroglia incubated with the relevant plasma sample and subjected to CSH treatment.

EXAMPLE 2

Demographics and HOS Activity in Normal Young Control (NYC), Normal Elderly Control (NEC), Mild Cognitive Impairment (MCI) and Sporadic Alzheimer Disease (AD) Subjects Results are shown in tabular form in FIG. 2. Suppression by 24 h incubation in human plasma of CSH-induced (880 µM×6 h) glial HO-1 mRNA band (Northern blot) relative to CSH-treated astrocytes grown in standard culture media; 0=0–25% suppression, 1=26–50% suppression, 2=51–75% suppression, 3=76–100% suppression. HOS=HOS activity; MMSE=Folstein Mini-mental State Exam Score Cortisol=Plasma cortisol levels (nMol/L). AD Meds=cholinesterase inhibitors used for treatment of Alzheimer disease. E400 and E800=400 and 800 units vitamin E, respectively C500=500 mg vitamin C. HOS activity was assayed as described in Example 1. Measurement of cortisol levels were performed using the GammaCoat [I-125] Cortisol Radioimmunoassay (RIA) Kit based on the competitive binding principles of RIA.

EXAMPLE 3

HOS Activity in Normal Control (NC), Mild Cognitive Impairment (MCI) and Sporadic Alzheimer Disease (AD) Subjects Results are shown in FIG. 3. HOS activity=percentage suppression (quartiles) by 24 h incubation in human plasma of CSH-induced (880 µM×6 h) glial HO-1 mRNA band (Northern blot) relative to CSH-treated astrocytes grown in standard culture media. HOS activity was assayed as described in Example 1.

EXAMPLE 4

Figure 4A:
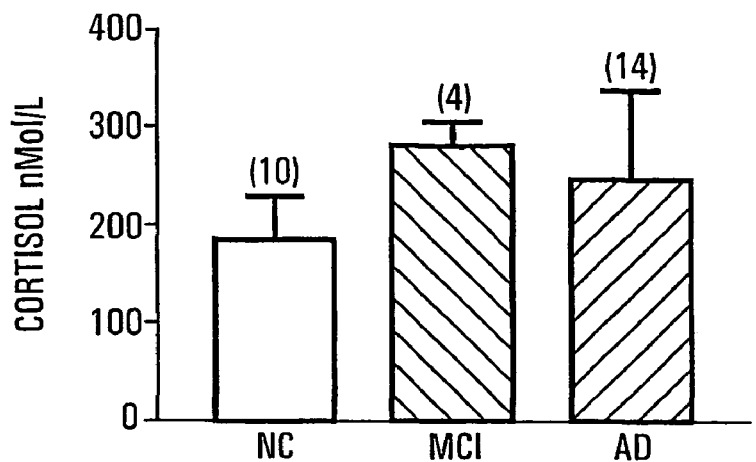
FIG. 4 depicts analysis of plasma cortisol levels (mean±SD) in normal control (NC), mild cognitive impairment (MCI) and sporadic Alzheimer disease (AD) subjects (panel A), as described in Example 4. ( )=number of cases per group. Differences between groups are not statistically significant (1-way ANOVA). Correlation between plasma cortisol levels and HOS activity in the MCI (panel B) and AD (panel C) groups is not significant (linear regression analysis).
Figure 4B:
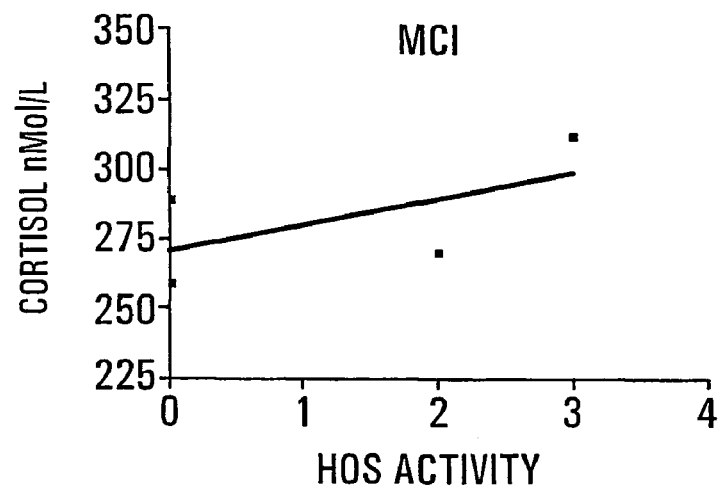
Figure 4C:
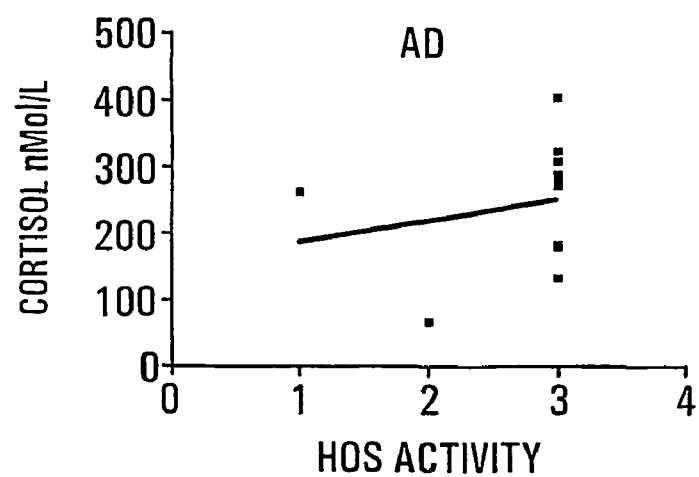

Plasma Cortisol Levels (Mean±SD) in Normal Control (NC), Mild Cognitive Impairment (MCI) and Sporadic Alzheimer Disease (AD) Subjects Results are shown in FIG. 4. Panel A shows mean (±SD) plasma cortisol levels of NC, MCI and AD subjects. ( )=number of cases per group. Differences between groups are not statistically significant (1-way ANOVA). Correlations between plasma cortisol levels and HOS activity in the MCI (panel B) and AD (panel C) groups are not significant (linear regression analysis). Although glucocorticoids are known suppressors of the HO-1 gene, these data indicate that elevated cortisol levels are not responsible for HOS activity in the MCI and AD plasma.

EXAMPLE 5

Effects of Sample Storage Time and Antioxidant Exposure on Plasma HOS Activity

Figure 5:
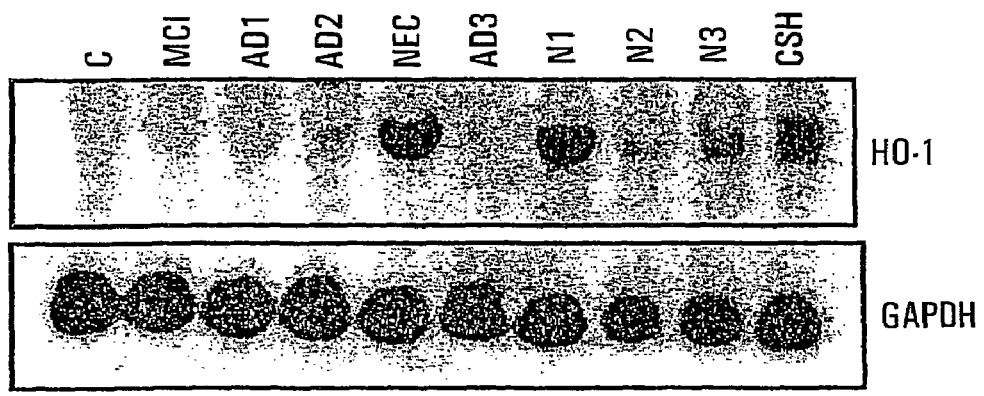
FIG. 5 is a Northern analysis of HO-1 mRNA demonstrating the effects of sample storage time and antioxidant exposure on plasma HOS activity, as described in Example 8. C=Control (untreated) astrocyte cultures, CSH=cysteamine-treated astrocyte culture, AD=Alzheimer, MCI=Mild Cognitive Impairment, NEC=normal elderly control, N=normal subject on antioxidants. Control GAPDH bands are used as noted in FIG. 1.

Results are shown in FIG. 5. HOS activity was assayed as described in Example 1. C=Control (untreated) astrocyte cultures, CSH=cysteamine-treated astrocyte culture, AD=Alzheimer, MCI=Mild Cognitive Impairment, NEC=normal elderly control, N=normal subject on antioxidants. Protease inhibitors (Complete Protease Inhibitor Cocktail, Cat. # 1836153, Roche, Mannheim) were added to all plasma samples prior to freezing. HOS activity is retained in AD and MCI plasma samples stored at −85 C for up to 15 months. In normal subjects, low-dose vitamin E (400 U/day), a dose of vitamin E commonly taken by AD patients, does not affect the astrocyte HO-1 mRNA response to CSH (N1). In normal individuals, exposure to multiple, very high-dose antioxidants partially attenuates the glial HO-1 mRNA response to CSH (N2, N3).

EXAMPLE 6

Effects of Plasma Dilution on HOS Activity

Plasma HOS activity was assayed via the determination of HO-1 mRNA levels in treated rat astroglia as described in Example 1. In this case, the effects of plasma dilution were examined, as documented in FIG. 6.

Lane 1: Absence of HO-1 mRNA in unchallenged rat astrocytes grown in standard culture media. Lane 2: Cysteamine (CSH 880 µM×6 h) induces strong HO-1 mRNA bands in cultured astroglia grown in standard media. Lane 3: Absence of HO-1 mRNA bands in unchallenged astrocytes grown in Alzheimer (AD) plasma (A: patient 1; B: patient 2). Lanes 4–6: undiluted AD plasma markedly suppresses the HO-1 mRNA response to CSH in cultured astroglia (intense HOS activity present). The glial HO-1 mRNA response to CSH progressively increases (abrogation of HOS activity) with increasing dilutions of AD plasma using standard media (lanes 7–15).

Figure 6A:
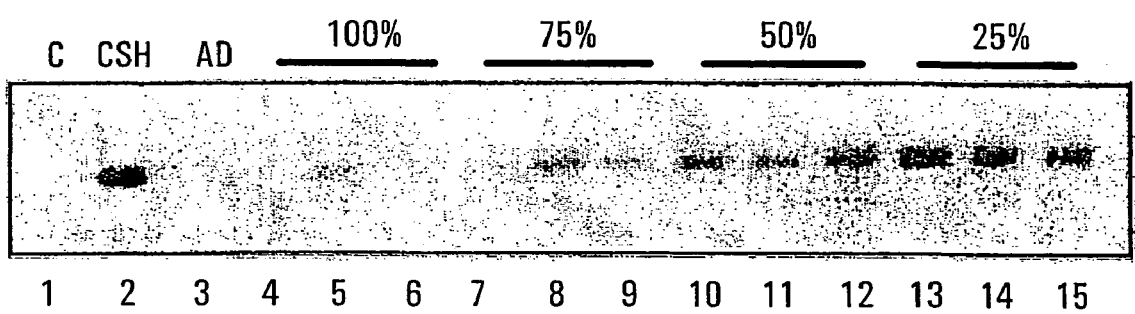
FIGS. 6A–6B Northern analysis of HO-1 mRNA demonstrating the effects of plasma dilution on HOS activity, as described in Example 6.
Figure 6B:
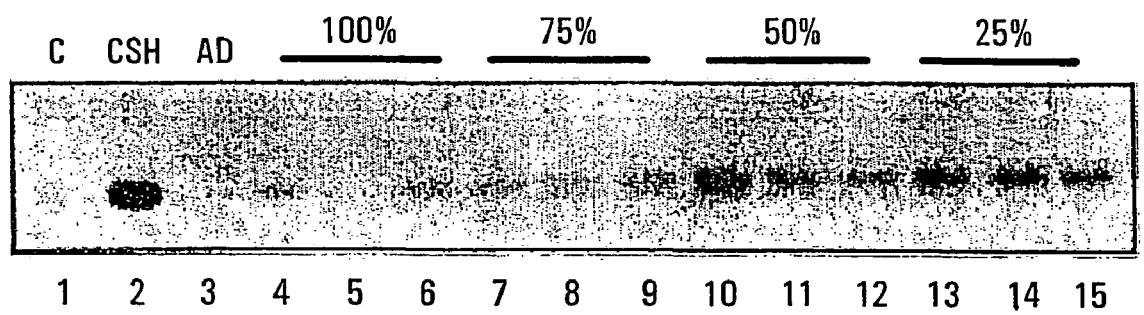

Panel A and panel B of FIG. 6 represent data obtained using plasma obtained from two different AD patients (A: patient 1; B: patient 2). As noted above and shown again in FIG. 6, untreated rat astroglia grown in standard culture media exhibit little or no detectable HO-1 mRNA (lane 1), however, HO-1 expression increases significantly upon CSH treatment (lane 2). In the absence of CSH treatment, rat astroglia incubated with AD plasma show no detectable HO-1 mRNA (lane 3), also as noted in Example 1. CSH treatment of rat astroglia incubated with undiluted AD plasma ("100%") failed to induce any significant induction of HO-1 expression (lanes 4–6), due to the intense HOS activity present in the undiluted AD plasma. However, the rat astroglial response to CSH progressively increases (abrogation of HOS activity) with increasing dilutions of the AD plasma using standard media (lanes 7–15). Therefore, there appears to exist in AD plasma a HOS factor whose plasma concentration correlates with HOS activity.

EXAMPLE 7

Effect of Heat Treatment on HOS Activity

Figure 7:
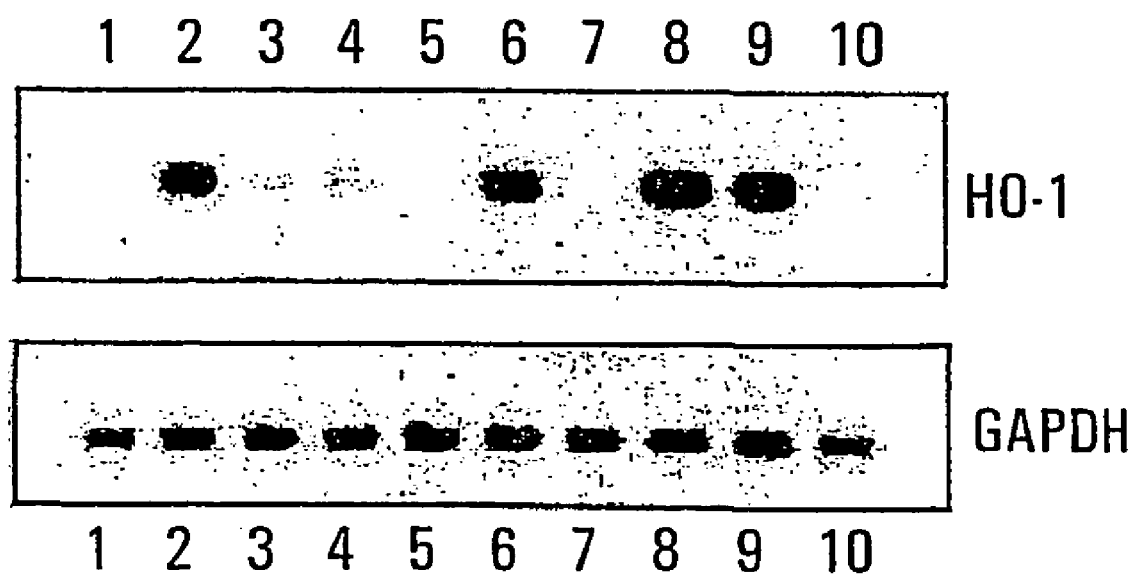
FIG. 7 is a Northern analysis of HO-1 mRNA demonstrating the effect of heat treatment on HOS activity, as described in Example 7. Control GAPDH bands are used as noted in FIG. 1.

Plasma HOS activity was assayed via the determination of HO-1 mRNA levels in treated rat astroglia as described in Example 1. In this case, the effects of prior heat treatment of AD plasma were examined, as documented in FIG. 7.

As noted above, control rat astroglia grown in standard media or exposed to human plasma (from normal [NEC] subjects or AD patients) exhibit little or no HO-1 mRNA via Northern analysis in the absence of CSH treatment (lanes 1, 5, 7 and 10). CSH treatment (880 µM CSH×6 h) of astroglia grown in standard media results in the observation of an intense HO-1 mRNA signal (lane 2). Also as noted above, this induction of HO-1 expression in response to CSH treatment is significantly attenuated in astroglia incubated in AD plasma for 24 h (lanes 3 and 4). However, this attenuation is no longer observed when the AD plasma is heated (100 C for 10 min.) prior to incubation with rat astroglia, indicating that as a result of this pre-heating AD plasma HOS activity is abrogated, as observed in the robust HO-1 mRNA signal seen in lane 6. CSH treatment of rat astroglia with normal plasma either untreated or pre-heated results in a robust observed HO-1 mRNA signal, since HOS activity is absent in either case (lanes 8 and 9). Therefore, these data indicate that HOS activity in AD plasma is mediated by a protein.

EXAMPLE 8

Partial Purification of HOS Factor by Heparin-Agarose Affinity Column Chromatography Plasma from one normal subject (NEC) and one AD patient (AD) was subjected to affinity purification on a heparin-agarose column as described in Sasaki et al. (1987), herein incorporated by reference, as follows:

Plasma preparation for loading onto Heparin Agarose column: The NEC and AD plasma tubes were thawed at 4 C. The samples were then dialyzed against Heparin Agarose column loading buffer [HALB: 20 mM Hepes (SIGMA Chemical Co., Saint Louis, Mich., USA, Catl # H-4034) pH 7.2, 150 mM NaCl, protease inhibitor tablet (Roche Diagnostics, Laval, PQ, CANADA Catl. # 1 873 580)] for 2 h with gentle stirring. The samples were then centrifuged at 15,000 g at 4 C for 20 minutes and supernatants collected.

Heparin Agarose affinity column chromatography: The Heparin Agarose column (1 cm×2 cm SIGMA Chemical Co., Saint Louis, Mich., USA, Catl # H-0402) was pre-washed with 20 ml of HALB. Plasma supernatants were loaded on the column. The column was washed with 4–6 volumes of HALB and 1 ml fractions collected. The flow-through fractions containing protein were pooled. The column was eluted with elution buffer [EB: 20 mM Hepes pH 7.2, 1 M NaCl, protease inhibitor] and 1 ml eluates containing proteins were pooled and dialyzed against HALB for 2–4 h.

The preparation of protein (e.g. plasma or column fractions) for the rat astroglia/HOS activity assay was performed as described in Sasaki et al. (1987), herein incorporated by reference, as follows:

Media was removed from 70 ml, 25 cm² flasks containing confluent astrocyte monolayer (7–10 days in culture). To each individual flask, 1.4 ml of NEC or AD plasma was added. To each individual flask, approximately 1.4 ml (10 mg protein based on the Bradford BioRad Protein assay kit using BSA as control) of the Heparin Agarose flow-through fraction derived from NEC or AD subjects was added with 0.6 ml of complete DMEM medium. To each individual flask, approximately 1.4 ml (0.5 mg protein) of the Heparin Agarose eluate fractions derived from NEC or AD subjects was added with 0.6 ml of complete DMEM medium.

Subsequently, the various samples were assayed for HOS activity as described in Example 1. Briefly, the eluate samples were incubated with rat astroglia, which were then subjected to CSH treatment. Subsequent mRNA isolation and Northern analysis to determine the level of HO-1 mRNA was performed, with the results shown in FIG. 8.

Figure 8:
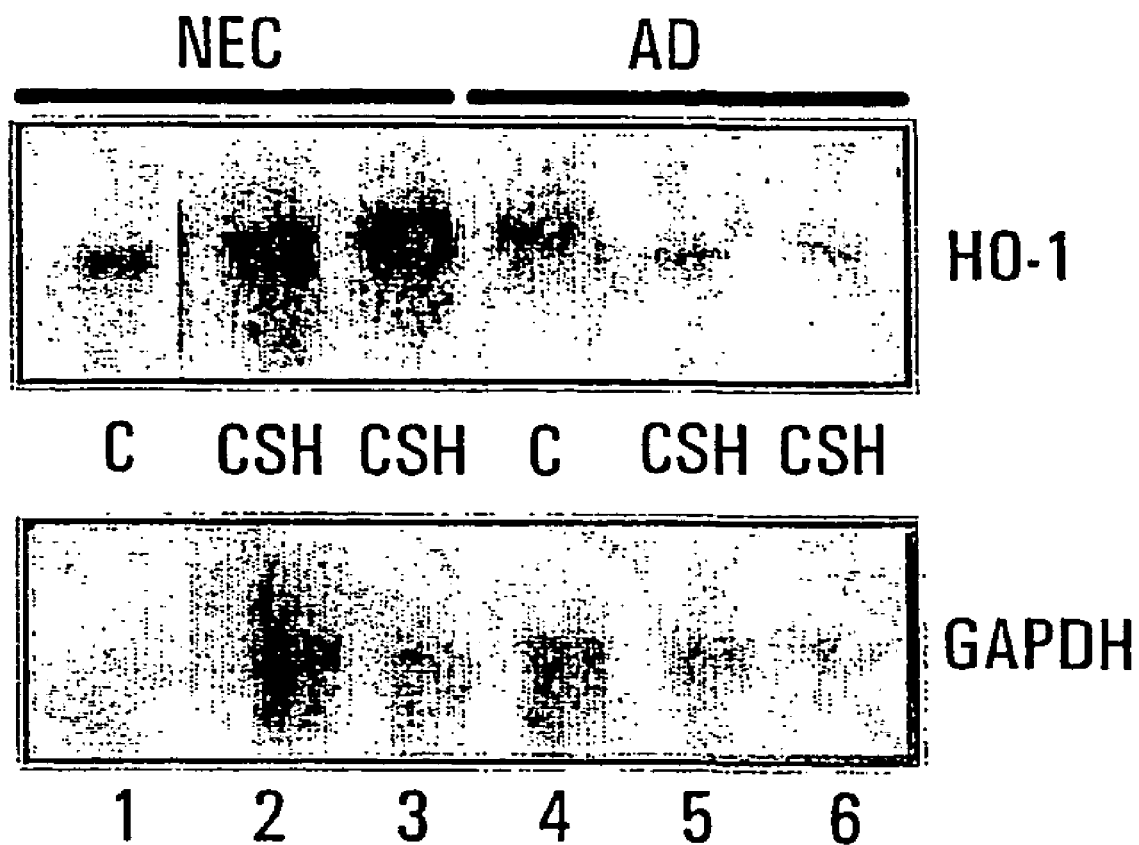
FIG. 8 is a Northern analysis of HO-1 mRNA demonstrating the partial purification of HOS factor by heparin-agarose chromatography, as described in Example 8. Control GAPDH bands are used as noted in FIG. 1.

FIG. 8: Panel A: Northern blots of HO-1 mRNA. Panel B: Control GAPDH mRNA. Plasma from one NEC and one AD patient was affinity purified on a heparin-agarose column and the eluate, collected using a high salt solution, was dialyzed. In the absence of CSH treatment, control rat astroglia pre-incubated with heparin eluates from NEC or AD plasma for 24 h did not exhibit an increase in HO-1 expression, as observed by the relatively faint HO-1 mRNA bands which correspond to these samples (lanes 1 and 4). CSH treatment (880 μM CSH×6 h) of rat astroglia incubated with the heparin eluate from NEC plasma results in an induction of HO-1 expression, as observed by intense HO-1 mRNA bands (lanes 2 and 3). Conversely, no augmentation of HO-1 mRNA bands in response to CSH treatment was observed in rat astroglia incubated for 24 h with the heparin eluate fraction derived from the plasma of the AD patient. These data support the presence of a HOS factor in the plasma of AD patients, but not normal (NEC) subjects, and indicate that the factor binds to heparin-agarose affinity columns.

EXAMPLE 9

Figure 9:
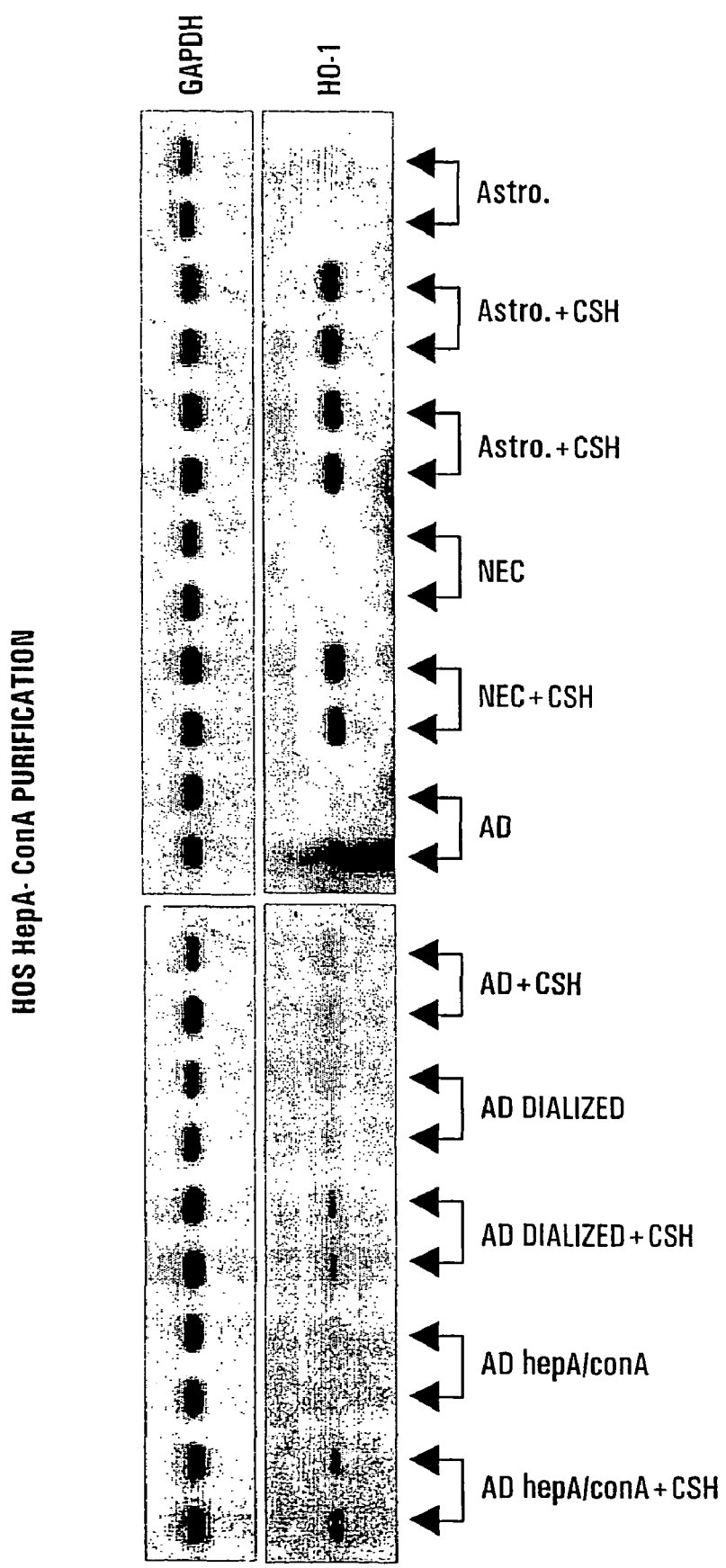
FIG. 9 is a Northern analysis of HO-1 mRNA demonstrating further HOS purification of the heparin agarose eluate by Concanavalin-A (Con-A) Agarose affinity column chromatography, as described in Example 9. Control GAPDH bands are used as noted in FIG. 1.

Further HOS Purification of Heparin Agarose Eluate by Concanavalin-A (Con-A) Agarose Affinity Column Chromatography Heparin Agarose column eluate (as described in FIG. 8) was dialyzed against loading buffer: 50 mM Hepes, pH 7.2 containing 150 mM NaCl, 1 mM $MgCl_2$, 1 mM $MnCl_2$, 1 mM $CaCl_2$ and Complete™ EDTA-free Protease inhibitor cocktail for 4 h at 4° C. The dialysate was loaded onto Con-A Agarose column. The column was washed with four bed volumes of loading buffer. The HOS fraction was eluted with loading buffer containing 0.2M α-D-methyl mannopyranoside. The eluate was dialyzed against loading buffer. The HOS bioassay (glial HO-1 mRNA response to 880 μM CSH×6 h) was performed as described in Example 1 and FIG. 1. Results are shown in FIG. 9. Glial HO-1 mRNA bands were faint in all specimens not exposed to CSH. Robust HO-1 mRNA responses to CSH were observed in control astroglial cultures (grown in standard culture media) and astrocytes incubated for 24 hours in NEC plasma. In contrast, HO-1 mRNA responses to CSH were markedly suppressed in astrocytes incubated for 24 hours in (i) whole AD plasma, (ii) dialyzed AD plasma prior to heparin-ConA chromatography and (iii) heparin Agarose-ConA eluate derived from AD plasma These data indicate that the AD plasma HOS factor binds to ConA columns and is therefore likely a glycoprotein.

EXAMPLE 10

Figure 10:
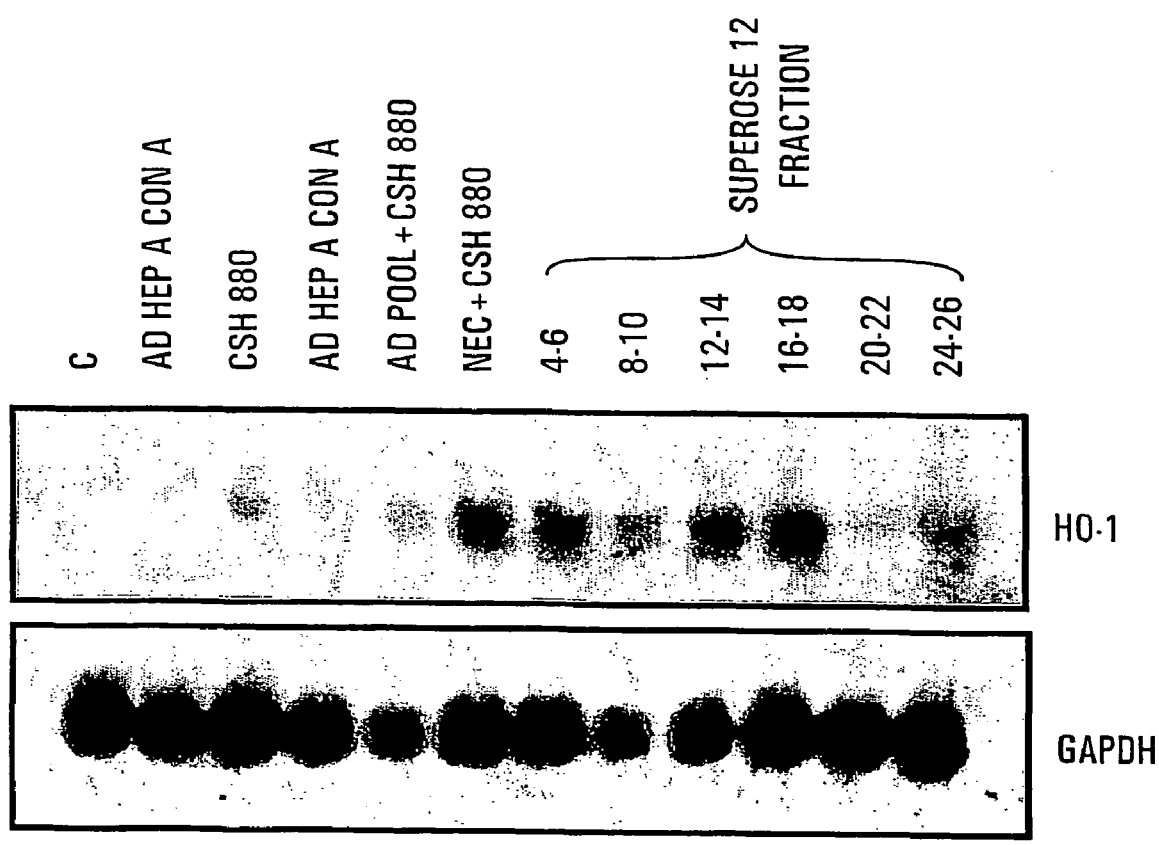
FIG. 10 is a Northern analysis of HO-1 mRNA demonstrating further HOS purification of the heparin agarose-conconavalin A eluate derived from 4 pooled AD plasma samples (29 cc starting material) on a Superose™ 12 HR FPLC Column, as described in Example 10. Control GAPDH bands are used as noted in FIG. 1.
Figure 11:
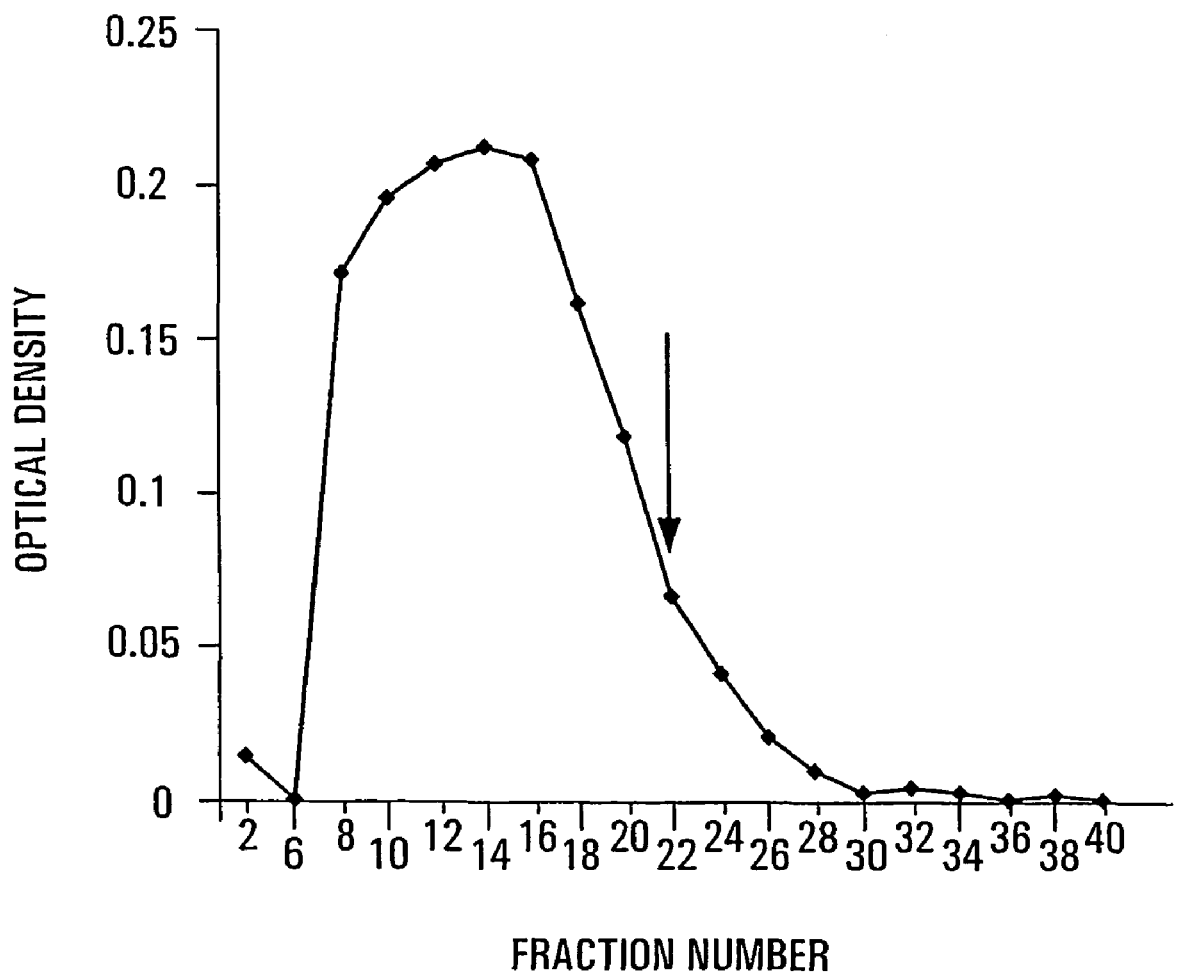
FIG. 11 presents graphical results of relative protein concentrations in Superose™ 12 HR FPLC Column fractions derived from pooled AD plasma samples described in FIG. 10, as described in Example 10. Arrow denotes protein concentration in fraction (number 20–22) exhibiting robust HOS activity.
Figure 12:
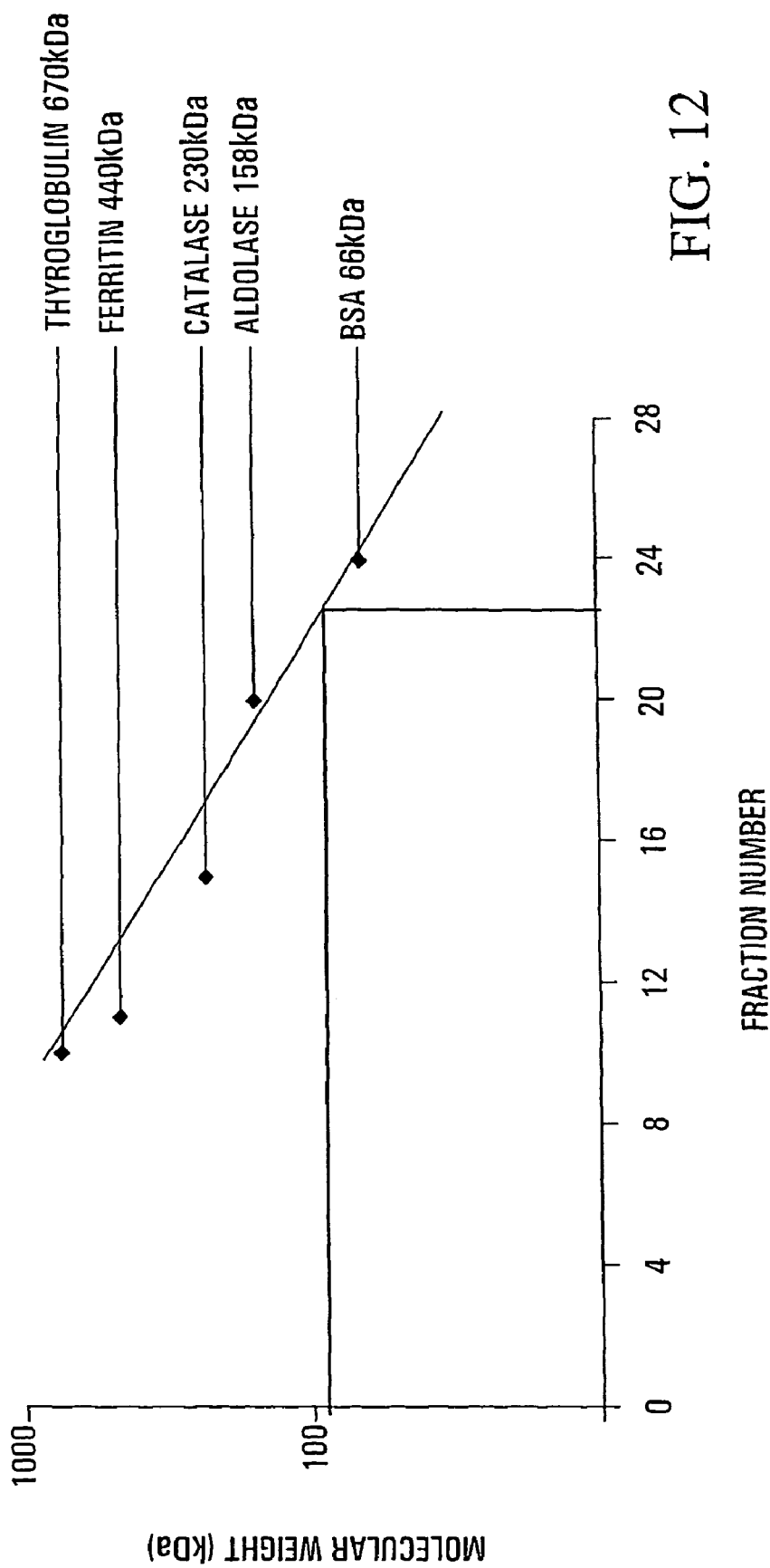
FIG. 12 depicts results of a chromatogram from a function test of Superose™ 12 HR FPLC 1-cm diameter column (Catl. # 17-0538-01, Lot # 8283034) [Amersham Pharmacia Biotech, Inc Quebec Canada] using standard protein mixtures, as described in Example 10.

Further HOS Purification of Heparin Agarosecon-Conavalin Eluate Derived from 4 Pooled AD Plasma Samples (29 cc Starting Material) on Superose™ 12 HR FPLC Column Results are shown in FIGS. 10 to 12. Heparin Agarose—ConA Agarose purified AD plasma (1-ml) was dialyzed against 20 mM Hepes, pH 7.2 containing 150 mM NaCl and Complete™ EDTA-free Protease inhibitor cocktail (1 tablet/100-ml; Catl. # 1873580, Lot 61320101, Roche Diagnostics, Quebec, Canada) for four hours at 4 C. The dialyzed fraction was loaded on Superose™ 12 HR FPLC 1-cm diameter column (Catl. # 17-0538-01, Lot # 8283034) [Amersham Pharmacia Biotech, Inc Quebec Canada]. HOS activity was measured by bioassay in each fraction as described in Example 1 and FIG. 1. As shown in FIG. 10, robust HOS activity was observed in fraction number 20–22.

FIG. 11: Relative protein concentrations in Superose™ 12 HR FPLC Column fractions derived from pooled AD plasma samples described in FIG. 10. Each 0.5-ml fraction of the flow-through was collected and absorbance (O.D.) measured at 280 nm by spectrophotometer. A graph of O.D. versus fraction number is plotted. Arrow denotes protein concentration in fraction (number 20–22) exhibiting robust HOS activity (FIG. 11).

FIG. 12: A chromatogram from a function test of Superose™ 12 HR FPLC 1-cm diameter column (Catl. # 17-0538-01, Lot # 8283034) [Amersham Pharmacia Biotech, Inc Quebec Canada] using standard protein mixtures. Plasma samples were derived from the same pooled AD plasmas described in FIG. 10. Each 0.5-ml fraction of the flow-through was collected and absorbance measured at 280 nm. A graph of peak molecular weight for each protein standard versus fraction number was plotted. Based on the elution profile of standards with known molecular weight, the molecular weight of the HOS-positive fraction (number 20–22) is estimated at approximately 90 kDa.

EXAMPLE 11

Figure 13:
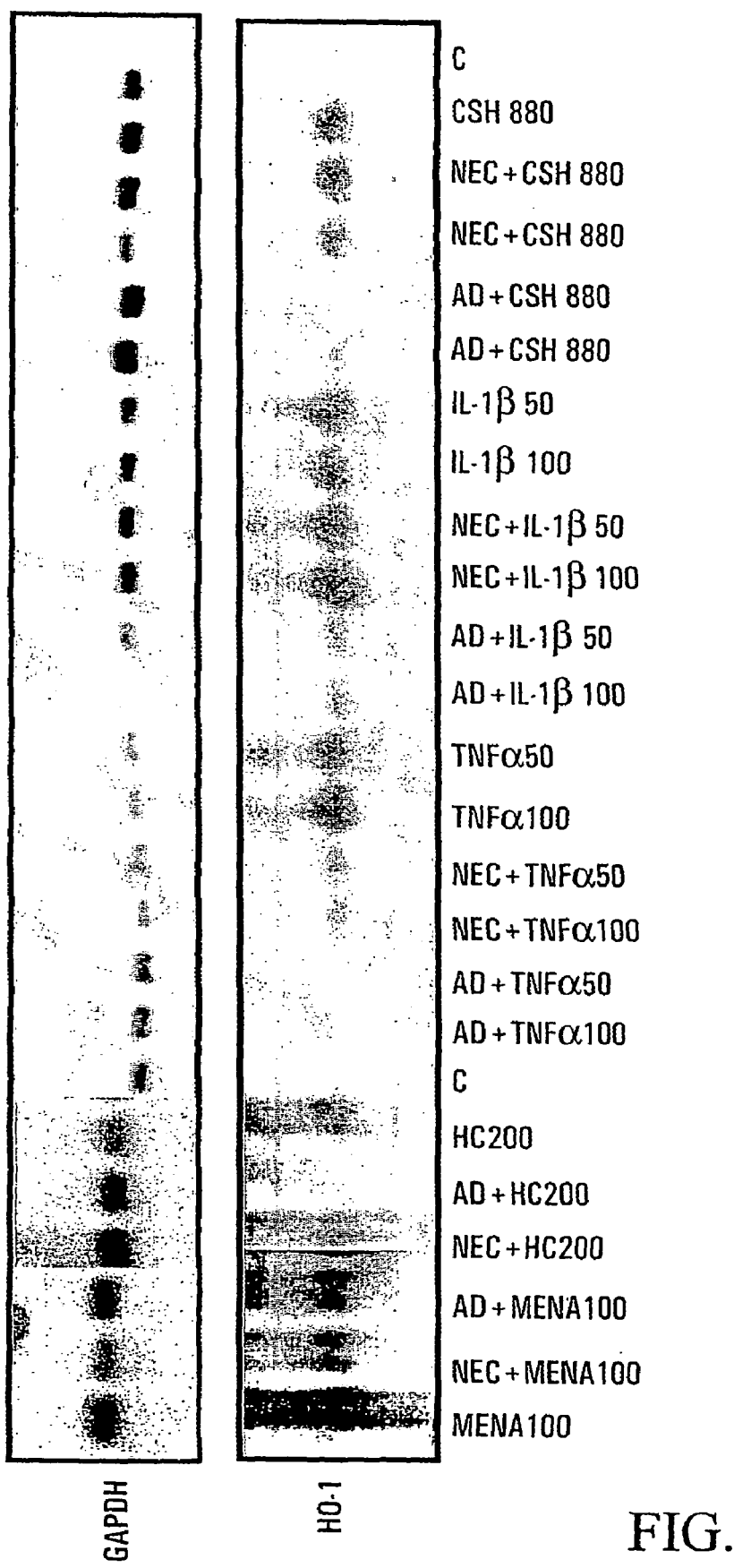
FIG. 13 is a Northern analysis of HO-1 mRNA demonstrating the effects of NEC and AD plasma on astrocyte HO-1 mRNA induction by multiple stimuli. The HOS bioassay was performed as described for FIG. 1. Northern blots for HO-1 mRNA (top) and respective GAPDH mRNA (bottom) are shown. Control GAPDH bands are used as noted in FIG. 1.

Effects of NEC and AD Plasma on Astrocyte HO-1 mRNA Induction by Multiple Stimuli The HOS bioassay was performed as described in Example 1 and FIG. 1. Northern blots for HO-1 mRNA (top) and respective GAPDH mRNA (bottom) are shown in FIG. 13. AD plasma strongly suppressed the HO-1 mRNA response to CSH (880 μM), interleukin-1β (Il-1β 50 and 100 ng/ml), and homocysteine (HC 200 μM). NEC plasma showed no HOS activity in the face of these stimuli. AD plasma completely suppressed, whereas NEC plasma partially suppressed, the HO-1 mRNA response to tumour necrosis factor-α (TNF-α 50 and 100 ng/ml). AD and NEC plasma exhibited partial and equal suppression of the glial HO-1 mRNA response to menadione (Mena 100 μM). These data indicate that: A) The HOS protein in AD plasma is active against multiple inducers of astroglial HO-1 mRNA. B) HOS activity in AD plasma is particularly potent in the face of TNF-α challenge. Since partial HOS activity against TNF-α also occurs in NEC plasma, differences in HOS protein expression between AD and NEC may be quantitative rather than qualitative. C) Simple antioxidant behavior does not account for HOS activity in AD plasma because both AD and NEC plasma exhibit partial and equal suppression of the glial HO-1 mRNA response to the pro-oxidant, menadione.

The above examples illustrate application of the testing method to detect HOS activity. Further, the above examples illustrate the testing method using plasma as the tissue or body fluid sample. The method can also be applied to other tissue or body fluids such as blood, cerebrospinal fluid, urine, saliva, epithelia and to fibroblast cell lines derived from patients.

The test can be applied to compare the level of HOS activity in a specific patient over a period of time, or to compare the level of HOS activity in a patient with the corresponding level in a normal control population.

The above examples further demonstrate the presence of a HOS factor which is a glycoprotein, in an embodiment a mannoprotein, having an approximate molecular weight in the range of 80–100 kDa, in an embodiment having a molecular weight of approximately 90 kDa, and which is not a glucocorticoid.

REFERENCES

Abraham, N. G. (1998) Quantitation of heme oxygenase (HO-1) copies in human tissue or body fluids by competitive RT/PCR, in *Methods in Molecular Biology, vol.* 108: *Free Radical and Antioxidant Protocols* (Armstrong, D., ed.), pp. 199–209, Humana Press Inc., Totowa, N.J.

Coligan J. E., et al., (1994) *Current Protocols in Immunology*, John Wiley & Sons, Inc., New York, N.Y.

Chomczynski P. and Sacchi N. (1987) Single-step method of RNA isolation by acid guanidinium thiocyanate-phenol-chlorophorm extraction. Analytical Biochem. 162:156–159.

Chopra, V. S., et al. (1995) Differential effects of cysteamine on heat shock protein induction and cytoplasmic granulation in astrocytes and glioma cells. Mol. Brain Res. 31:173–184.

Chopra, V. S., et al. (1997) A cellular stress model for the differential expression of glial lysosomal cathepsins in the aging nervous system. Exp. Neurol. 147:221–228.

Church G. M. and Gilbert W. (1984) Genomic sequencing. Proc. Natl. Acad. Sci. USA 81:1991–1995.

Deramaudt, T. B., et al. (1999) Negative regulation of human heme oxygenase in microvessel endothelial cells by dexamethasone. Proc. Soc. Exp. Biol. Med. 222:185–193.

Feinberg A P and Vogelstein B. (1984) A Technique for radiolabelling DNA restriction endonuclease fragments to high specific activity. Analytical Biochem. 137:266–267.

Grossi, D., et al. (1988) Senile dementias. II International Symposium (pp. 97–99). Paris: John Libbey Eurotext.

Harlow, E. and Lane, D (1988) *Antibodies: A Laboratory Manual*, Cold Spring Harbor Laboratory Press, Cold Spring Harbor, N.Y.

Haxby J. V., et al. (1992) Individual trajectories of cognitive decline in patients with dementia of the Alzheimer type. J. Clin. Exp. Neuropsychol. 14:575–592.

Kohler G. and Milstein C. (1975) Continuous cultures of fused cells secreting antibody of predefined specificity. Nature 256:495–497.

Lavrovsky, Y., et al. (1996) Downregulation of the human heme oxygenase gene by glucocorticoids and identification of 56b regulatory elements. Biochem. Biophys. Res. Comm. 218:759–765.

Mann, U., et al. (1992) Heterogeneity in Alzheimer's disease: Progression rate segregated by distinct neuropsychological and cerebral metabolic profiles. J. Neurol. Neurosurg. Psychiatry 55:956–959.

Mawal, Y., et al. (2000) RT-PCR confirmation of suppressed HO-1 mRNA levels in Alzheimer lymphocytes. Abstract to be presented at the 1st International Symposium on HO/CO, Jul. 14–17, 2000.

Noonberg S. B., et al. (1994) Detection of triplex-forming RNA oligonucleotides by triplex blotting. BioTechniques 16:1070–1072.

Sasaki, H., et al., (1987) Improved method for the immobilization of heparin. J. Chromatog. 400:123–132.

Schipper H. M., et al. (1995). Expression of heme oxygenase-1 in the senescent and Alzheimer-diseased brain. Ann. Neurol. 37:758–768.

Schipper H. M., et al. (1999) Mitochondrial iron sequestration in dopamine-challenged astroglia: role of heme oxygenase-1 and the permeability transition pore. J. Neurochem. 72:1802–1811.

Schipper H. M., et al. (2000) Evaluation of Heme Oxygenase-1 as a Systemic Biological Marker in AD. Neurology 54:1297–1304.

Yelton D. E. and Scharff M. D. (1981) Monoclonal Antibodies: a powerful new tool in biology and medicine. Ann. Rev. Biochem. 50:657–680.

The invention claimed is:

1. A heme oxygenase-1 suppressor (HOS) factor, said HOS factor having the activity of attenuating an increase in heme oxygenase-1 (HO-1) occurring in response to exposure to an experimental agent or treatment of oxidative stress, said HOS factor by:
 subjecting a tissue or body fluid sample derived from a patient suffering from a dementing disease to affinity chromatography using one or a sequential combination of a heparin-agarose column, a concanavallin-A (Con-A) agarose column, or a Superose™-12 column;
 eluting fractions of the sample and selecting those fractions containing protein having a molecular weight in the range of 80–100 kDa as determined from an elution profile of protein standards with known molecular weight; and
 assaying the selected fractions eluted from affinity chromatography for HOS activity by assessing ex vivo the capacity of said fractions to attenuate an increase in the level of heme oxygenase-1 (HO-1) occurring in response to an experimental agent or treatment of oxidative stress, wherein said HOS factor maintains attenuation of HO-1 activity even when exposed to an antioxidant.

2. The HOS factor according to claim 1, wherein the eluted fractions of the sample are selected to contain protein having a molecular weight of 90 kDa as determined from an elution profile of protein standards with known molecular weight.

3. The HOS factor according to claim 1, wherein the sample is derived from a patient with Alzheimer disease.

4. The HOS factor of claim 1 wherein the HOS factor substantially binds to the heparin-agarose column under conditions of 20 mM Hepes pH 7.2, 150 mM NaCl, and is substantially eluted from the heparin-agarose column under conditions of 20 mM Hepes pH 7.2, 1M NaCl.

5. The HOS factor of claim 1, wherein the exposure to an experimental agent or treatment of oxidative stress comprises exposure to one or more of metal ions, amino acid analogues, sulfhydryl agents, interleukin-1β(IL-1β), tumour necrosis factor-α (TNF-α) or hyperthermia.

6. The HOS factor of claim 1, wherein the sulfhydryl agent is cysteamine or homocysteine.

7. The HOS factor of claim 6, wherein the sulfhydryl agent is cysteamine.

8. A method for assessing dementing diseases in a patient comprising:
 determining the level of heme oxygenase-1 suppressor (HOS) factor or activity, in tissue or a body fluid obtained from a patient; and
 comparing said level of HOS factor or activity with the corresponding level of HOS factor or activity in corresponding tissue or body fluid obtained from at least one control person, whereby if said level of HOS factor or activity is greater than said corresponding level of HOS factor or activity in said tissue or body fluid obtained from at least one control person then said patient suffers from a dementing disease;
 wherein such method is used to predict the onset of, diagnose, or prognosticate dementing diseases.

9. The method according to claim 8 wherein the tissue or body fluid is selected from blood, plasma, lymphocytes, cerebrospinal fluid, urine, saliva, epithelia and fibroblasts.

10. The method according to claim 8 wherein the dementing disease is selected from the group consisting of Alzheimer Disease, Age-Associated Cognitive Decline, Mild Cognitive Impairment, Parkinson disease with dementia, Progressive Supranuclear Palsy, Vascular (i.e. multi-infarct) Dementia, Lewy Body Dementia, Huntington's Disease, Down's syndrome, normal pressure hydrocephalus, corticobasal ganglionic degeneration, multisystem atrophy, head trauma, neurosyphilis, Creutzfeld-Jacob disease and other prion diseases, HIV and other encephalitides, and metabolic disorders such as hypothyroidism and vitamin B12 deficiency.

11. The method of claim 8 wherein the control person is a normal age-matched person.

12. The method of claim 8 wherein the method is used to prognosticate dementing diseases and wherein the control person is the patient from whom the corresponding tissue or body fluid was obtained at another time.

13. A commercial package comprising means for determining the level of HOS factor or activity as defined in claim 1, in tissue or body fluid obtained from a patient, and instructions for comparing said level of HOS factor or activity with an established standard of the corresponding HOS activity in a corresponding control tissue or body fluid.

14. The commercial package of claim 13 for use in a method for assessing dementing diseases in a patient.

15. A medicament comprising the HOS factor as defined in claim 1 in combination with a pharmaceutically acceptable carrier, for the treatment of a dementing disease.

* * * * *

UNITED STATES PATENT AND TRADEMARK OFFICE
CERTIFICATE OF CORRECTION

| | | |
|---|---|---|
| PATENT NO. | : 7,105,485 B2 | Page 1 of 1 |
| APPLICATION NO. | : 10/333880 | |
| DATED | : September 12, 2006 | |
| INVENTOR(S) | : Hyman M. Schipper | |

It is certified that error appears in the above-identified patent and that said Letters Patent is hereby corrected as shown below:

Column 23, line 9, claim 1, "...HOS factor by..." should be --...HOS factor obtained by...--.

Signed and Sealed this

Twenty-ninth Day of May, 2007

JON W. DUDAS
*Director of the United States Patent and Trademark Office*